(12) United States Patent
Turner et al.

(10) Patent No.: US 9,993,294 B2
(45) Date of Patent: Jun. 12, 2018

(54) MICROWAVE COAGULATION APPLICATOR AND SYSTEM WITH FLUID INJECTION

(75) Inventors: Paul F. Turner, Bountiful, UT (US); Thomas L. Youd, Salt Lake City, UT (US)

(73) Assignee: PERSEON CORPORATION, Salt Lake City, UT (US)

( * ) Notice: Subject to any disclaimer, the term of this patent is extended or adjusted under 35 U.S.C. 154(b) by 1517 days.

(21) Appl. No.: 12/794,667

(22) Filed: Jun. 4, 2010

(65) Prior Publication Data

US 2011/0118724 A1    May 19, 2011

Related U.S. Application Data

(63) Continuation-in-part of application No. 12/689,195, filed on Jan. 18, 2010, now Pat. No. 8,551,083, which
(Continued)

(51) Int. Cl.
*A61B 18/18* (2006.01)
*A61B 18/00* (2006.01)

(52) U.S. Cl.
CPC ............ *A61B 18/1815* (2013.01); *A61B 2018/00023* (2013.01); *A61B 2018/00029* (2013.01);
(Continued)

(58) Field of Classification Search
CPC ...... A61B 18/1815; A61B 2018/00023; A61B 2018/00029; A61B 2018/00577;
(Continued)

(56) References Cited

U.S. PATENT DOCUMENTS 3,598,108 A    8/1971  Jamshidi
4,397,314 A    8/1983  Vaguine
(Continued)

FOREIGN PATENT DOCUMENTS

CN    1676176 A    10/2005
EP    0207729       1/1987
(Continued)

OTHER PUBLICATIONS

U.S. Appl. No. 12/620,002, filed Nov. 17, 2009; Paul F. Turner; office action dated Aug. 17, 2012.
(Continued)

*Primary Examiner* — Michael Peffley
*Assistant Examiner* — Samantha Good
(74) *Attorney, Agent, or Firm* — Dinsmore & Shohl LLP

(57) ABSTRACT

A microwave applicator for insertion into living body tissue for use in microwave coagulation and ablation treatments includes a microwave transmission line extending between an attachment end of the applicator and an antenna toward an insertion end of the applicator with an outer conductive sleeve forming an enclosed fluid space around the transmission line. A fluid circulation system circulates fluid in the fluid space. A portion of or all of the circulating fluid can be injected into tissue that surrounds the applicator body from approximately the proximal end of a desired heating zone produced by microwave energy radiated from the antenna along the applicator body toward the proximal end of the applicator to hydrate and wet the tissue outside the proximal end of the desired heating zone to reduce the drying of this tissue and limit extension of the heating and ablation zone proximally along the applicator body.

20 Claims, 19 Drawing Sheets

Related U.S. Application Data is a continuation-in-part of application No. 12/620,002, filed on Nov. 17, 2009, now Pat. No. 8,414,570.

(52) U.S. Cl.
CPC .............. *A61B 2018/00577* (2013.01); *A61B 2018/00589* (2013.01); *A61B 2018/00815* (2013.01); *A61B 2018/1869* (2013.01); *A61B 2018/1892* (2013.01)

(58) Field of Classification Search
CPC .. A61B 2018/00589; A61B 2018/1869; A61B 2018/1892
USPC .............................. 606/32–33; 607/100–102
See application file for complete search history.

(56) References Cited

U.S. PATENT DOCUMENTS

| | | | |
|---|---|---|---|
| 4,448,198 A | 5/1984 | Turner | |
| 4,565,200 A | 1/1986 | Cosman | |
| 4,586,516 A | 5/1986 | Turner | |
| 4,638,436 A | 1/1987 | Badger et al. | |
| 4,669,475 A | 6/1987 | Turner | |
| 4,712,559 A | 12/1987 | Turner | |
| 4,825,880 A | 5/1989 | Stauffer et al. | |
| 4,860,752 A | 8/1989 | Turner | |
| 4,967,765 A | 11/1990 | Turner et al. | |
| 5,205,289 A | 4/1993 | Hardy et al. | |
| 5,275,597 A | 1/1994 | Higgins et al. | |
| 5,370,675 A | 12/1994 | Edwards et al. | |
| 5,405,346 A | 4/1995 | Grundy et al. | |
| 5,470,308 A | 11/1995 | Edwards et al. | |
| 5,507,743 A | 4/1996 | Edwards et al. | |
| 5,599,295 A | 2/1997 | Rosen et al. | |
| 5,607,389 A | 3/1997 | Edwards et al. | |
| 5,628,771 A | 5/1997 | Mizukawa et al. | |
| 5,683,384 A | 11/1997 | Gough et al. | |
| 5,720,718 A | 2/1998 | Rosen et al. | |
| 5,807,395 A | 9/1998 | Mulier et al. | |
| 5,853,366 A | 12/1998 | Dowlatshahi | |
| 5,861,002 A | 1/1999 | Desai | |
| 5,974,343 A | 10/1999 | Brevard et al. | |
| 5,976,129 A * | 11/1999 | Desai .............................. | 606/40 |
| 6,027,501 A | 2/2000 | Goble et al. | |
| 6,036,698 A | 3/2000 | Fawzi et al. | |
| 6,051,018 A | 4/2000 | Larsen | |
| 6,066,134 A | 5/2000 | Eggers et al. | |
| 6,106,524 A | 8/2000 | Eggers et al. | |
| 6,112,123 A | 8/2000 | Kellecher et al. | |
| 6,131,577 A | 10/2000 | Nicholson | |
| 6,136,014 A | 10/2000 | Sirimanne et al. | |
| 6,146,378 A | 11/2000 | Mikus et al. | |
| 6,162,216 A | 12/2000 | Guziak et al. | |
| 6,162,261 A | 12/2000 | Kempter et al. | |
| 6,178,354 B1 | 1/2001 | Gibson | |
| 6,275,738 B1 | 8/2001 | Kasevich et al. | |
| 6,306,132 B1 | 10/2001 | Moorman et al. | |
| 6,325,796 B1 | 12/2001 | Berube et al. | |
| 6,347,251 B1 | 2/2002 | Deng | |
| 6,355,033 B1 | 3/2002 | Moorman et al. | |
| 6,358,273 B1 | 3/2002 | Strul et al. | |
| 6,427,089 B1 | 7/2002 | Knowlton | |
| 6,471,709 B1 | 10/2002 | Fawzi et al. | |
| 6,582,426 B2 | 6/2003 | Morrman et al. | |
| RE38,299 E | 11/2003 | Bolmsjo | |
| 6,652,516 B1 | 11/2003 | Gough | |
| 6,652,520 B2 | 11/2003 | Moorman et al. | |
| 6,752,767 B2 | 6/2004 | Turovskiy et al. | |
| 6,770,070 B1 | 8/2004 | Balbierz | |
| 6,868,290 B2 | 3/2005 | Bolmsjo | |
| 6,878,147 B2 | 4/2005 | Prakash et al. | |
| 6,962,586 B2 | 11/2005 | Berube et al. | |
| 6,962,589 B2 | 11/2005 | Muller et al. | |
| 6,974,454 B2 | 12/2005 | Hooven et al. | |
| 7,001,415 B2 | 2/2006 | Hooven | |
| 7,101,369 B2 | 9/2006 | Van der Welde | |
| 7,128,739 B2 | 10/2006 | Prakash et al. | |
| 7,147,632 B2 | 12/2006 | Prakash et al. | |
| 7,160,292 B2 | 1/2007 | Moorman et al. | |
| 7,311,703 B2 | 12/2007 | Turovskiy et al. | |
| 7,318,824 B2 | 1/2008 | Prakash et al. | |
| 7,344,533 B2 | 3/2008 | Pearson et al. | |
| 7,527,623 B2 | 5/2009 | Prakash et al. | |
| 7,594,313 B2 | 9/2009 | Prakash et al. | |
| 7,594,913 B2 | 9/2009 | Ormsby et al. | |
| 7,699,841 B2 | 4/2010 | Carr | |
| 7,799,019 B2 | 9/2010 | Turovskiy et al. | |
| 7,862,559 B2 | 1/2011 | Prakash et al. | |
| 7,863,984 B1 | 1/2011 | Behnke | |
| 7,875,024 B2 | 1/2011 | Turovskiy et al. | |
| 8,414,570 B2 * | 4/2013 | Turner et al. .................. | 606/33 |
| 2001/0001819 A1 | 5/2001 | Lee et al. | |
| 2003/0023238 A1 | 1/2003 | Manker et al. | |
| 2003/0060813 A1 | 3/2003 | Loeb et al. | |
| 2003/0212394 A1 | 11/2003 | Pearson et al. | |
| 2004/0049254 A1 | 3/2004 | Longo | |
| 2004/0181214 A1 | 9/2004 | Garabedian et al. | |
| 2005/0015081 A1 | 1/2005 | Turovskiy et al. | |
| 2005/0085881 A1 | 4/2005 | Prakash et al. | |
| 2005/0245920 A1 | 11/2005 | Vitullo et al. | |
| 2006/0004351 A1 | 1/2006 | Arless et al. | |
| 2006/0122593 A1 | 6/2006 | Jun | |
| 2007/0288079 A1 | 12/2007 | Van der Weide et al. | |
| 2008/0033422 A1 | 2/2008 | Turner et al. | |
| 2008/0033424 A1 | 2/2008 | Van der Weide et al. | |
| 2008/0033434 A1 | 2/2008 | Boomer et al. | |
| 2008/0045938 A1 | 2/2008 | Van der Weide | |
| 2008/0135217 A1 | 6/2008 | Turovskiy et al. | |
| 2008/0161890 A1 | 7/2008 | Lafontaine | |
| 2008/0275436 A1 * | 11/2008 | Cronin et al. .................. | 606/33 |
| 2009/0005766 A1 | 1/2009 | Brannan | |
| 2009/0131926 A1 | 5/2009 | Rusin et al. | |
| 2009/0248006 A1 | 10/2009 | Paulus et al. | |
| 2010/0087808 A1 | 4/2010 | Paulus | |
| 2010/0228244 A1 * | 9/2010 | Hancock ............ | A61B 18/1815 606/33 |
| 2011/0118723 A1 * | 5/2011 | Turner et al. .................. | 606/33 |

FOREIGN PATENT DOCUMENTS

| | | |
|---|---|---|
| JP | S62-5364 A | 1/1987 |
| JP | S62-32975 A | 2/1987 |
| JP | H03-3358 A | 1/1991 |
| JP | 2004/187703 A | 7/2004 |
| JP | 2004-187704 A | 7/2004 |
| JP | 2009/521967 A | 6/2009 |
| RU | 2063697 C1 | 7/1996 |
| SU | 1676633 A1 | 9/1991 |
| WO | WO 98/06341 | 2/1998 |
| WO | WO 00/56239 | 9/2000 |
| WO | WO 2007/076924 A2 | 7/2007 |
| WO | WO 2011/063061 A2 | 5/2011 |

OTHER PUBLICATIONS

U.S. Appl. No. 12/689,195, filed Jan. 18, 2010; Paul F. Turner; office action dated Aug. 31, 2012.

Murakami et al.; Treatment of Hepatocellular Carcinoma: Value of Percutaneous Microwave Coagulation; AJF, 1995; vol. 164; pp. 1159-1164.

Drozd et al.; Comparison of Coaxial Dipole Antennas for Applications in the Near-field and Far-field Regions, Microwave Journal; 2004; 7 pages. Reprinted with permission of Microwave Journal from the May 2004 Issue, 2004 Horizon House Publications, Inc.

Short et al.; Physical Hyperthermia and Cancer Therapy, Proceedings of the IEE; Jan. 1980; pp. 133-142; vol. 68, No. 1.

Gottlieb et al.; Interstitial Microwave Hyperthermia Applicators having Submillimeter Diameters, Int. J. Hyperthermia; 1990; pp. 707-714; vol. 6, No. 3.

(56) References Cited

OTHER PUBLICATIONS

Iskander et al.; Design Optimization of Interstitial Antennas; IEEE Transactions on Biomedical Engineering; Feb. 1989; pp. 238-246; vol. 36, No. 2.
Bourgeois et al., Cancer Therapy by Hyperthermia and Radiation, 1978, pp. 121-124, Urban & Schwarzenberg, Baltimore-Munich.
Jones et al., Theoretical and Experimental SAR Distributions for Interstitial Dipole Antenna Arrays Used in Hyperthermia, IEEE Transactions on Microwave Theory and Techniques, Aug. 1989, pp. 1200-1209, vol. 37, No. 8.
Sieyes et al., Some aspects of optimization of an invasive microwave antenna for local hyperthermia treatment of cancer, Med. Phys., Mar./Apr. 1981, pp. 174-183, 8(2).
Trembly et al., Comparison of Power Deposition by In-Phase 433 MHz and Phase-Modulated 915 MHz Interstitial Antenna Array Hyperthermia Systems, IEEE Transactions on Microwave Theory and Techniques, May 1988, pp. 908, vol. 36, No. 5.
Denman et al., The Distribution of Power and Heat Produced by Interstitial Microwave Antenna Arrays: II The Role of Antenna Spacing and Insertion Depth, Int. J. Radiation Oncology Biol. Phys., Sep. 1987, pp. 537-545, vol. 14.
Furse et al. Three-Dimensional Electromagnetic Power Deposition in Tumors Using Interstitial Antenna Arrays, IEEE Transactions on Biomedical Engineering, Oct. 1989, pp. 977-986, vol. 36, No. 10.
Iskander et al., Evaluation and Optimization of the Electromagnetic Performance of Interstitial Antennas for Hyperthermia, Int. J. Radiation Oncology Biol. Phys., Oct. 1989, pp. 895-902, vol. 18.
Turner, Paul F., Interstitial Equal-Phased Arrays for EM Hyperthermia, IEEE Transactions on Microwave Theory and Techniques, May 1986, pp. 572-578, vol. MTT-34, No. 5.
B. Stuart Trembly et al., Control of the SAR Pattern within an Interstitial Microwave Array through Variation of Antenna Driving Phase, IEEE Transactions on Microwave Theory and Techniques, 1986, 568-571, vol. MTT-34, No. 5.
Chopra, Rajiv et al. Method for MRI-guided conformal thermal therapy of prostate with planar transurethral heating applicators. Oct. 13, 2005. Institute of Physics Publishing. Physics in Medicine and Biology 50 (2005) pp. 4957-4975.
Related Case: U.S. Appl. No. 12/620,022, filed Nov. 17, 2009; Paul F. Turner.
Related Case: U.S. Appl. No. 12/689,195, filed Jan. 18, 2010; Paul F. Turner.
Related Case: U.S. Appl. No. 13/020,483, filed Feb. 3, 2011; Paul F. Turner.
PCT Application PCT/US2010/057127; filed Nov. 17, 2010; Paul Turner; International Search Report dated Aug. 25, 2011.
U.S. Appl. No. 12/689,195, filed Jan. 18, 2010; Paul F. Turner; notice of allowance dated May 29, 2013.
Stauffer et al., Interstitial Heating Technologies, Thermoradiotheray and Thermochemotherapy, pp. 279-320, vol. 1, Jun. 1995.

\* cited by examiner

US 9,993,294 B2

MICROWAVE COAGULATION APPLICATOR AND SYSTEM WITH FLUID INJECTION

RELATED APPLICATIONS

This is a continuation-in-part of application Ser. No. 12/620,002, filed Nov. 17, 2009, now U.S. Pat. No. 8,414,570, and of application Ser. No. 12/689,195, filed Jan. 18, 2010, now U.S. Pat. No. 8,551,083, both entitled Microwave Coagulation Applicator and System, and both hereby incorporated herein by reference.

BACKGROUND OF THE INVENTION

Field

This invention relates to electromagnetic radiation (EMR) therapy and more particularly to applicators and systems for applying electromagnetic energy to a treatment site in a living body to heat tissue needing treatment at the treatment site. The invention is useful particularly for treatments in the nature of microwave coagulation or ablation. A limitation found in current microwave antennas that are used for microwave coagulation and ablation is that the energy distribution pattern generally extends back along the applicator from the proximal end of the desired coagulation and ablation zone around the microwave energy radiating portion of the applicator toward the proximal end of the applicator. This undesirably extends the coagulation and ablation zone along the applicator toward the proximal end of the applicator beyond the tissue desired to be coagulated or ablated. This results in an elliptical or tear drop heating pattern shape where the desired shape for the energy distribution pattern and the coagulation and ablation zone is generally more spherical.

State of the Art

The use of electromagnetic (EM) energy to heat tissue for the treatment of disease is known. In using microwave energy for tissue heating, an applicator having a microwave radiating antenna is positioned with respect to the tissue to be treated (heated) so that microwave energy radiated from the antenna penetrates and heats the tissue. Many microwave applicators are known in the art. Death, or necrosis, of living tissue cells occurs at temperatures elevated above a normal cell temperature for a sufficient period of time. The sufficient period of time is generally dependent upon the temperature to which the cells are heated. Above a threshold temperature of about 41.5 degrees C., substantial thermal damage occurs in most malignant cells. At temperatures above about 45 degrees C. thermal damage occurs to most normal cells. During treatment, it is desirable to produce an elevated temperature within the targeted tissue for a time period sufficient to cause the desired cell damage, while keeping nearby healthy tissue at a safe lower temperature. For this reason, when treatment involving tissue heating is used, it is important to assure both adequate tumor heating throughout the tumor to the tumor margin and reduced temperatures in the critical normal tissue.

Heating therapy is sometimes combined with other treatments, such as surgery, ionizing radiation, and chemotherapy. For example, when heating is combined with radiation, it is desirable to maintain the temperature within the diseased tissue within the range of about 42 to 45 degrees C. Higher temperatures are usually undesirable when a combined treatment modality is used because higher temperatures can lead to microvessel collapse causing resistance to radiation therapy and decrease the amount of systemic chemotherapy from reaching the tumor if it has vascular damage. Lower temperatures are undesirable because they can fail to provide adequate therapeutic effect. Therefore, it is important to control the temperature within the desired range for multi-modality treatments and not allow heating of the tissue in the tumor or around the tumor to above 45 degrees C. if such tissue damage from other treatments may be compromised. Treatment within this controlled temperature range is usually referred to as hyperthermia.

Forms of thermal therapy that kill the tissue with heating alone are generally referred to as coagulation or ablation. To adequately eradicate a cancerous tumor with only the application of heat, it is necessary to ensure adequate heating is accomplished throughout the entire tumor. In cases of a malignant tumor, if viable tumor cells are left behind, the tumor can rapidly grow back leaving the patient with the original problem. In what is generally referred to as microwave coagulation or microwave ablation, the diseased tissue is heated to at least about 55 degrees C., and typically above about 60 degrees C., for exposure times sufficient to kill the cells, typically for greater than about one minute. With microwave coagulation and ablation treatments, there is a volume reduction of temperature that ranges from the high temperature in the treated tissue to the normal tissue temperature of 37 degrees C. outside the treated tissue. The outer margin of the overall heat distribution in the treated tissue volume may then result in damage to normal tissue if such normal tissue is overheated. Therefore, for prolonged coagulation or ablation treatments where the coagulation or ablation volume is maintained at very high temperatures, there is a high risk of damage to surrounding normal tissues. For proper treatment of targeted cancerous tumor volumes or other tissue volumes to be treated, it becomes very important to properly deliver the correct thermal distribution over a sufficient time period to eradicate the tumor tissue while minimizing damage to critical surrounding normal tissue. Fortunately, there are tumor locations that reside in normal tissue that can be destroyed by the heating in limited areas without affecting the health of the patient, such as liver tissue. In such situations the coagulation can be applied in an aggressive way to include a margin of safety in destruction of limited surrounding normal tissues to assure that all of the cancerous tumor is destroyed.

The process of heating very rapidly to high temperatures that is common in coagulation and ablation treatments may utilize a rather short exposure time. In doing so, the resulting temperature distribution becomes primarily a result of the power absorption distribution within the tissue. However, if such treatments continue for multiple minutes, the blood flow and thermal conduction of the tumor and surrounding tissues will modify the temperature distribution to result in a less predictable heat distribution because the changes occurring in blood flow in such a heated region may not be predictable. Thus, it is important to optimize the uniformity of the tissue heating power that is absorbed to lead to a more predictable temperature distribution that better corresponds with the treatment prescription. Therefore, pretreatment planning practices prior to and possibly during treatment for calculating the power and temperature distribution resulting from the parameters of power and relative phase of the power applied to the tissue can be important for not only coagulation and ablation, but also hyperthermia. As higher temperatures are used during treatment, it may increase patient discomfort and pain, so it can be helpful to avoid excessive temperatures to reduce the need of patient sedation.

Invasive microwave energy applicators can be inserted into living body tissue to place the source of heating into or adjacent to a diseased tissue area. Invasive applicators help to overcome some difficulties that surface applicators experience when the target tissue region is located below the skin (e.g., the prostrate). Invasive applicators must be properly placed to localize the heating to the vicinity of the desired treatment area. Even when properly placed, however, it has been difficult to ensure that adequate heat is developed in the diseased tissue without overheating surrounding healthy tissue. Further, with applicators operating at higher power levels to produce the needed higher temperatures for coagulation and ablation, there is a tendency for the coaxial cable in the portion of the applicator leading from outside the body to the location of the radiating antenna in the applicator to heat to undesirably high temperatures which can cause thermal damage to the normal tissue through which the applicator passes to reach the diseased tissue to be treated. Therefore, various ways of cooling the applicator have been used in the prior art.

In the use of radiofrequency (RF) electrodes in the prior art, a primary electrode is invasively inserted into the body while a secondary electrode is either invasively inserted into the body such as in a bipolar RF applicator or separately at another location or is placed on the skin outside the body so that radio frequency heating currents pass from the primary electrode to the secondary electrode. In this process, the tissue around the primary electrode has the tendency to dry out and char. When the tissue around the primary electrode that needs to pass the RF heating currents to the secondary electrode dries, the drying of the tissue around the electrode provides high electrical resistance to impede the flow of heating current. This drying of the tissue then limits the flow of current from the primary electrode out into the tissue beyond the dry or charred tissue thereby limiting the tissue coagulation zone to that which is achieved prior to the formation of this dry or charred tissue around the electrode. A technique has been developed to infuse fluid, such as saline solution, from the tip of such primary RF electrode to permit the tissue fluids to be replaced as they are being heated in that region, thereby reducing the resistance to current flow by maintaining the wetness and the electrical conductivity of the tissue near the electrode. This allows continued desired flow of current from the primary electrode to produce the desired tissue heating and coagulation. Examples of this are shown in U.S. Pat. Nos. 6,066,134, 6,112,123, and 6,131,577. It is also known in the art that fluids, such as saline solution, can be used with microwave antennas where the infusion of the fluids, such as saline, is introduced into the primary heating region to aid in the maintenance of the radiation impedance of the antenna by replacing the fluids in the tissue in the area of primary radiation and heating. Examples of this are shown in published patent applications 2006/0122593 and 2009/0248006. Other methods are also utilized to improve the impedance matching during microwave coagulation of tissue such as tuning changes by frequency change (U.S. Pat. No. 7,594, 913) and variation of the exposed radiating antenna tip (published application 2009/0131926).

It is also known that with microwave energy applicators, the radiated energy forms a tear-drop type heating pattern with a tail extending back along the applicator shaft from the desired tissue heating zone into the normal tissue along the applicator insertion path toward the proximal end of the applicator. In some instances, the extent of the tail changes during treatment and with the positioning of the applicator, such as with the insertion depth of the applicator. The forming of this heated tail and the alteration of the coagulation zone as a function of variable insertion depths is not a desirable result as the coagulation zone should be consistent at various reasonable insertion depths, and the heating zone produced by the applicator is desirably a more spherical shape to produce a more spherical ablation zone.

While many microwave applicators are known in the art for applying microwave energy to tissue to provide heating to the tissue, there is a need for better applicators that are easy to use, have more consistent and predictable heating and coagulation patterns, and particularly that are able to limit the length of the energy absorption pattern and the heating zone to limit the elongation along the applicator proximally from the desired heating zone to therefore provide, when used for coagulation or ablation, a more spherical coagulation or ablation shape.

SUMMARY OF THE INVENTION

The inventors theorize that the tail of the heating zone produced by a microwave antenna which is caused by microwave energy extending along the applicator toward the proximal end of the applicator from the proximal end of the desired heating zone, and the often continuing extension of this tail along the applicator during the application of microwave energy, is caused by the drying of the tissue, first in the desired heating and ablation zone around the microwave antenna, and then along the applicator body from the desired heating zone toward the proximal end of the applicator. The theory is that as the tissue dries around the desired heating zone, the dielectric constant of the tissue decreases and the wavelength of the microwave energy in the tissue increases. As the wavelength of the microwave energy in the tissue increases, the area heated by the energy increases along the applicator toward the proximal end and causes heating of the tissue in this new area into which the longer microwaves are extending. This heating dries this tissue to further extend the wave length of the microwaves in this area which further extends the heating area along the applicator shaft, thus heating more and more of the tissue along the applicator shaft toward the proximal end of the shaft along the insertion path of the applicator. In addition, or alternately, when the tissue dries and reduces the dielectric constant value of the tissue, there is a higher amount of the radiated electric field that is concentrated in the drying tissue that surrounds the proximal outer portion of the applicator, which outer portion is usually formed by a metal outer shaft. This is due to the fact that the distribution of the electric field that is perpendicular to the metal of the metal shaft and is inversely proportional to the value of the dielectric constant of the respective tissue, varies with the boundaries between the wet and dry tissue. This means that the electric field lines that pass perpendicularly through the drying tissue layers to the perpendicular metal shaft are altered in their distribution relative to the tissues. For example, if the dielectric value of the tissue around the shaft is reduced by a factor of 10, as can be caused by charring, there would be a factor of 10 increase in the electric field strength in that dry and charred region that would not be attenuated as rapidly compared to that of non-dry tissues as it propagates along the outer metal body of the applicator toward the proximal end. This could further increase the length of the tapering tail of the heating or ablation zone in the tissue along the proximal body portion of the applicator.

According to the invention, the inventors have found that by supplying fluid, such as a saline solution, to the tissue along the applicator shaft extending from approximately the proximal end of the desired heating zone toward the proximal end of the applicator to replace the fluid in such tissue and preventing the drying of such tissue, that the tail of the heating zone is limited and that it is maintained substantially constant rather than increasing with increased heating time. Thus, by injecting fluid into the tissue along the applicator shaft extending from approximately the proximal end of the desired heating zone toward the proximal end of the applicator, the tissue in this area maintains its moisture content and limits the distance the tail extends along the applicator and substantially prevents the continuing elongation of the tail during the heating time. As a result, the heating and ablation zone becomes less tear drop shaped and more spherical shaped. This occurs without the necessity of injecting fluid into the desired heating zone and even though the tissue in the desired heating zone therefore will dry during heating. With fluid injection into the tissue in the area indicated outside and proximal to the desired heating zone, the applicator can be designed and tuned to produce a substantially constant heating and ablation zone. Fluid can be supplied to the tissue in various ways. If the applicator includes an applicator fluid cooling system, the fluid injected into the tissue may be a portion of the cooling fluid from the applicator cooling system that is directed from the cooling system into the tissue, or, with or without a fluid cooling system, fluid may be provided specifically and directly to the tissue to keep it in a moistened condition.

An embodiment of microwave applicator according to the invention for use in microwave coagulation and ablation treatments includes an elongate applicator body having an insertion (distal) end for insertion into a tissue region of a living body and an attachment (proximal) end for attachment to a source of microwave energy. An antenna for radiating microwave energy into tissue to be treated to produce a desired heating and ablation zone in the tissue is disposed toward the insertion end of the elongate applicator body. A coaxial microwave energy transmission line is disposed within the applicator body to conduct microwave energy from the attachment end of the applicator to the antenna. In order to limit the extent to which the microwave energy extends along the applicator from approximately the proximal end of the desired heating and ablation zone toward the proximal end of the applicator, thereby limiting the usual tail of the heating and ablation zone along the applicator toward the proximal end of the applicator, fluid can be injected along the applicator from approximately the proximal end of the desired heating zone a distance along the applicator body toward the proximal end of the applicator. By injecting fluid in this tissue region, tissue moisture and a higher dielectric constant is maintained in the tissue to maintain a higher microwave loss factor so that the microwave energy radiated into this tissue region is more rapidly attenuated as it travels along the outside of the inserted applicator. This feature aids in providing a more spherical coagulation pattern by reducing the energy that extends along the applicator extending through the tissue region that is not intended to be heated.

In one embodiment of the applicator which includes a fluid cooling system, an outer conductive sleeve forms the outside of a portion of the applicator body and is spaced concentrically around the microwave energy transmission line to form a cooling fluid space between the inside surface of the outer conductive sleeve and the outer surface of the microwave energy transmission line. The cooling fluid space extends from the proximal end of the applicator to the approximate proximal end of the desired heating and ablation zone. Because cooling is not normally needed in the tissue to be heated during coagulation and ablation treatments, cooling is not provided in the area of the radiating antenna of the applicator where the heating of tissue is desired. A guide sleeve is positioned concentrically within the cooling fluid space and spaced inwardly from the outer conductive sleeve and around the outside of and spaced outwardly from the microwave energy transmission line. The guide sleeve guides flow of a circulating cooling fluid along the outside surface of the microwave energy transmission line and the inside surface of the outer conductive sleeve to cool the microwave energy transmission line and the conductive outer sleeve to maintain the portion of the applicator extending between the outside of the living body and the tissue to be treated in the living body at a temperature below that which will damage healthy tissue. For fluid injection, the distal region of the cooling fluid space may be configured with one or more openings through the outer conductive sleeve to permit a portion of the cooling fluid that circulates in the cooling fluid space to leak into or be injected into the tissue surrounding this region that is proximal to the desired heating and ablation zone to reduce the drying out of tissue in that region. This reduces the formation of the tear-drop type tail extending from the desired heating and ablation zone around the antenna. The added fluid in the tissue proximal the desired heating and ablation zone maintains a higher tissue moisture content in that proximal region which maintains a higher tissue dielectric constant in that region and higher microwave loss factor so that the portion of the microwave energy radiated is more rapidly attenuated as it travels along the outside of the inserted shaft. This provision of fluid to the tissue thereby limits the energy that extends along the applicator proximally from the desired heating and ablation zone into the area not intended to be heated, so limits the creation of the heated tail and results in a more spherical heating and ablation pattern.

With the fluid cooled applicator, a pump is generally provided to circulate the cooling fluid through the cooling fluid space. The fluid pressure of the pump will generally provide sufficient hydraulic pressure to force a small amount of fluid through the openings through the outer conductive sleeve into the tissues. The typical flow rate of cooling fluid in the cooling fluid space within the applicator body is in the range of 20 to 40 ml/minute. The rate needed to infuse fluid into the tissue in the inserted proximal portion of the applicator would be in the range of less than 10 ml/minute and typically in the range of 1 to 6 ml/minute. Therefore, there is ample flow to permit such a small volume to pass into the tissue without significant changes to the applicator shaft cooling system and the inner circulation of cooling fluid through the applicator. A temperature sensor is positioned to measure the approximate temperature of the circulating cooling fluid thereby indicating that cooling fluid is actually circulating in the cooling fluid space and that the microwave energy transmission line and the outer conductive sleeve are being actively cooled during the microwave coagulation or ablation treatment. By monitoring the approximate temperature of the cooling fluid, the heating of the tissue along the insertion track of the applicator where inserted into the living body to the diseased tissue can be better controlled to ensure that damage to surrounding normal tissue is minimized during treatments. Further, when fluid is injected into the tissue from the cooling fluid circulation system, confirmation of circulation of cooling fluid also confirms that fluid is being infused or injected into the tissue surrounding the portion of the applicator proximal the desired heating and ablation zone.

Alternately, rather than circulating cooling fluid in the applicator, infusion of fluid into the tissue may be provided by eliminating the fluid flow return path either by blocking the fluid return path or removing the fluid return path inside the applicator body, or by providing a direct fluid flow path opening to the tissue, and providing either a lower flow rate pump to provide the fluid directly to the tissue or by providing a fluid gravity drip line that is typical of intravenous (IV) fluid applications. In such a case the fluid flow rate can be set to a predetermined flow rate that would be typically in the range of 1 to 6 ml/minute.

In one embodiment of the present invention, a microwave applicator for heat treatment of diseased tissue within a living body includes a handle by which the applicator can be held and manipulated for insertion into the living body. An elongate applicator body having an insertion end for insertion into a tissue region of the living body extends from the handle which usually forms the attachment end of the applicator. An antenna is disposed toward the insertion end of the applicator body. Microwave energy is conducted from the handle to the antenna via a microwave energy transmission line in the form of a coaxial cable disposed within the applicator body. The coaxial cable includes an inner conductor and an outer conductor separated by a dielectric material therebetween. An outer conductive sleeve extends from the handle to an insertion end of the outer conductive sleeve which is separated from the conductive tip by a gap, usually filled with a dielectric material. The outside diameters of the insertion tip, the outer conductive sleeve, and the dielectric material filling the gap therebetween are all about equal so as to form a substantially smooth continuous elongate applicator body, for insertion into the living body. The elongate applicator body, or at least the portion thereof to be inserted into a living body, may be coated with a stick resistant dielectric material such as Teflon. This can at least partially reduce the sticking of coagulation tissue to the applicator outer surface, particularly in the areas of tissue coagulation and ablation, to facilitate removal of the applicator after treatment. However, in one embodiment of the applicator, a portion of the dielectric material separating the conductive tip and the outer conductive sleeve remains exposed for direct contact with heated tissue. The dielectric material is a material, such as PEEK (polyetheretherketone), that heated tissue will stick to. This is a relatively small area along the applicator, but upon heating, the tissue will stick to this dielectric material and such sticking will stabilize the applicator to keep it in position during treatment of the tissue. When removal of the applicator is desired, the applicator can be rotated, such as through between thirty and forty-five degrees of rotation, to release the tissue and permit removal of the applicator.

In the illustrated example embodiment, the elongate applicator body extending from the handle will be substantially rigid. The outer conductive sleeve may be made of a metal such as stainless steel. The conductive insertion tip of the applicator will also be metal, such as brass or stainless steel, and may be sharpened sufficiently so that the applicator can be inserted directly into tissue to be treated. However, even when sharpened, the applicator will generally not be inserted directly through the tough tissue of the skin, but will usually require that a cut or an opening, such as made by a hypodermic needle inserted through the skin, first be made and then the applicator is inserted through such cut or opening. Further, in an illustrated example embodiment, a conductive metal shunt is positioned at the insertion end of the conductive outer sleeve to extend toward the insertion tip. The shunt is also electrically coupled to the outer conductor of the microwave energy transmission line, thereby electrically coupling the outer conductor of the microwave energy transmission line to the conductive outer sleeve. The insertion tip is secured to, but separated from, the insertion end of the shunt by a substantially rigid dielectric spacer that has structural stiffness to prevent bending of the joint between the shunt and tip and to electrically insulate the tip, which is electrically coupled to the microwave energy transmission line inner conductor, from the shunt, which is electrically coupled to the microwave energy transmission line outer conductor. The substantially rigid dielectric spacer is bonded to the shunt and applicator tip, such as by an epoxy adhesive. In another illustrated example embodiment, the shunt is not used and the dielectric material connects the conductive tip to the outer conductive sleeve. In this example embodiment, the outer conductive sleeve is electrically insulated from both the outer conductive tip and the outer conductor of the microwave energy transmission line.

A non-conductive guide sleeve extends from the handle and is positioned concentrically within the elongate applicator body inside and spaced inwardly from the outer conductive sleeve and around the outside of and spaced outwardly from the microwave energy transmission line, i.e., outwardly from the outer conductor thereof. The guide sleeve guides flow of a circulating cooling fluid from the handle along the outside surface of the coaxial microwave transmission line to the end of the guide sleeve toward the insertion end of the applicator, around the end of the guide sleeve, and back along the inside surface of the outer conductive sleeve to the handle. An opposite flow of the cooling fluid can also be used. Circulation of cooling fluid cools the coaxial microwave transmission line and the conductive sleeve to maintain the portion of the applicator extending between the outside of the living body and the tissue to be treated in the living body at a temperature below that which will damage healthy tissue. If fluid injection into tissue is desired, the outer conductive sleeve and/or the shunt may be provided with one or more openings therethrough to allow a portion of the cooling fluid when circulating in the applicator to flow from the applicator into the tissue surrounding the applicator adjacent the proximal end of the desired heating and ablation zone created by the applicator and extending a distance from the proximal end of the desired heating and ablation zone toward the proximal end of the applicator. The one or more openings are sized and positioned so as to allow substantially a predetermined amount of fluid flow into the tissue during fluid circulation in the applicator to maintain moisture in the tissue during operation of the applicator. A temperature sensor is positioned, such as in the handle, to measure the approximate temperature of the cooling fluid being circulated in the applicator. The temperature of the cooling fluid in the applicator is an indication of whether or not the fluid circulation system is operating and whether it is cooling sufficiently.

Supply and return connections for the cooling fluid from a pressurized source of cooling fluid, usually through flexible hoses, are provided in the handle. Also, a connection to connect to a source of microwave power, such as through a flexible coaxial cable, is also provided in the handle. The handle serves as an interface between the more flexible coaxial cable extending from a microwave generator and the more flexible fluid hoses from a source of cooling fluid, and the substantial rigid elongate applicator. In one example embodiment, a sheath is provided to enclose the hoses and flexible coaxial cable as they extend from the handle to keep them together and make handling of the applicator easier. An embodiment of the sheath material is a plastic braid material that will tighten around the enclosed hoses and coaxial cable when stretched.

The temperature sensor used in the applicator may be a thermistor. The resistance of a thermistor varies with the temperature of the thermistor. The temperature measured by the thermistor is obtained by an external circuit that measures the temperature by causing a constant dc current to flow through the thermistor. The resistance of the thermistor then produces a dc voltage that is indicative of the temperature of the thermistor. The temperature sensor in the handle, or a temperature sensor positioned along the applicator, may be coupled to the flexible coaxial cable extending from the microwave generator through a coupling network, such as a resistive and capacitive coupling network. The resistive and capacitive coupling network allows a dc current from the coaxial cable conductors to flow to and from the thermistor while isolating the thermistor from the microwave power signals, and allows the microwave power signals to flow to the antenna while isolating the antenna from the dc current. Similarly, a coupling network can be used at the opposite end of the flexible coaxial cable, such as in power splitting and multiplexing circuitry, to separate the dc temperature signals from the flexible coaxial cable conductors and direct them to temperature sensing circuitry in a system controller while isolating the temperature sensing circuitry from the microwave power signals, and passing the microwave power signals from the system microwave generator while isolating the system microwave generator from the dc temperature signals. The use of a computer in the system controller to sense forward power, reflected power, measure the thermistor temperature, and possibly monitor other variables such as monitoring tissue temperature by one or more independently inserted temperature sensors, provides control and feedback for the applied microwave power and the proper safety and operation of the microwave coagulation or ablation procedure.

In addition to the temperature sensor to measure the approximate temperature of the cooling fluid line in the applicator, one or more temperature sensors may be placed along the elongate applicator body so as to place the one or more temperature sensors at positions to measure the temperature of the tissue of the living body along the applicator. If such additional temperature sensors are provided, it is usually advantageous to position one of such temperature sensors at a position close to an expected outer margin of the desired or allowable heating area in the living body tissue to be heated by the antenna during operation of the applicator. This can be used to provide a warning if the tissue to be protected outside the margin of the area to be treated is approaching an undesirably high temperature. It can also be used to estimate the location of the outer margin of the effective heated volume during treatment.

The use of phased arrays can also reduce microwave heating along the shafts of the applicators due to cross coupling of the energy between the antennas that are driven in phase and separated by a distance that provides for partial power cancellation along the outer portion of the inserted applicators and an increase in tissue heating between these inserted applicators. This partial power cancellation is accomplished when the distance between approximately parallel inserted antennas is approximately a half of a wavelength so that the cross coupled energy is somewhat out of phase with that on an antenna due to its own radiated energy. For a frequency of 915 MHz, for example, the wavelength in typical high water content tissues, such as muscle and tumor tissues, is approximately 4.3 to 4.7 cm. This means that for an insertion separation of 2.1 to 2.4 cm the separation is about right for this 180 degree relationship. There is also cross coupled phase cancellation for significant phase differences other than 180 degrees, for example, a 135 or 225 degree phase difference will still provide partial phase cancellation from the cross coupling of the microwave coupled fields to partially cancel microwave energy along the outer portion of the inserted applicators. This would be consistent with an applicator spacing of between about 1.6 to 3.0 cm for the 915 MHz example. This partial cancellation of microwave power around the inserted shafts results in reduced heating along the inserted shafts during active microwave tissue heating. This also reduces the local power fields locally around the radiating antennas and the outer shafts to reduce tissue sticking to the antennas and shafts.

The control of the heating may further include the systematic use of applicators in phased arrays with optimization computational guidance in the form of pretreatment planning to provide an ideal insertion pattern and power and phase application to the array of applicators to produce and control improved uniformity of power deposition, temperatures, and/or coagulation of tissue throughout the tumor volume, and particularly at the tumor margins. The treatment is thereby optimized and controlled by the aid of a numerical calculation of either the planned insertion pattern and number of antennas or the actual pattern achieved as indicated by various non-invasive imaging processes such as computer tomography (CT), ultrasound, or magnetic resonance imaging (MRI). It also may be feasible to use such planning information to adjust power amplitude and phase of each of the inserted applicators as directed by a computer-controlled system using the predicted power patterns from the computer numerical model.

In a phased array embodiment of the invention, a single microwave generator is used to provide the microwave power for all applicators. The generator will usually operate at 915 MHz, which is an emission frequency commonly licensed for medical applications. This single generator is connected to a passive, non-switching, microwave impedance matched power splitter (divider) which is used to direct power simultaneously to multiple ports that are connected to one or more microwave dipole antennas such as described for the above described applicators. This arrangement provides approximately equal power simultaneously to each of the output connection ports. This arrangement also provides equal phase output of the microwave energy at each of the output ports. Thus, when multiple antennas are connected to the ports of the power splitter, they have equal power and equal relative phase and are thus correctly called a phased array of antennas. The cables going to the radiating points on each antenna are maintained at the same electrical length so that the radiated energy from the antennas are phase synchronous and phase coherent. Phase synchronous meaning that there is a fixed phase relationship between the radiation phase of all antennas and phase coherent meaning that the relative radiated phase from each antenna is approximately the same. The use of phased arrays as described increases the heating in the spaces between the antennas by providing improved uniformity of the coagulation of the targeted tissue providing more power absorption than when using channel switching and other non-phase synchronous and non-simultaneous channel operation methods.

When using a phased array of applicators, the applicator antennas are inserted in approximately a pattern than corresponds with equal spacing along the circumference of an insertion circle around the tissue to be treated. This provides for approximately equal spacing between the antennas along the perimeter of an insertion pattern. Thus, a pattern of two antennas would be inserted at a distance of separation that would represent the diameter of an insertion circle. Three antennas would form a triangle pattern as they are approximately equally spaced around the circumference of a circular insertion pattern. Four antennas would form a square pattern. The antennas should be approximately parallel as inserted with the central point of the radiation from each antenna inserted to approximately the same depth position with respect to the tissue to be treated so as to have the radiation feedpoints approximately aligned side by side.

As indicated, the applicator of the invention can be used as a single applicator inserted into the diseased tissue, or as an array of more than one applicator positioned in or around the diseased tissue. In order to provide the most efficient transfer of microwave energy from the microwave generator to the tissue to be treated, the flow paths of the microwave energy from the microwave generator to the applicator antennas should be impedance matched and tuned for the number of applicators used. This can require different systems with different power splitters when a single applicator is used or when multiple applicators are used to form an array. The present invention can provide a special power splitter circuit so that a single system can be used for a single applicator or for a plurality of applicators. According to the invention, at least one power splitter circuit is provided for coupling the microwave energy generator to at least one coaxial microwave energy supply cable for supplying microwave energy from the microwave generator to the microwave applicator. The at least one power splitter circuit has a microwave power input connected to the microwave generator and a plurality of output ports, wherein one of the plurality of output ports is a single connection output port for use where only a single coaxial microwave energy supply cable and microwave applicator is connected to the power splitter circuit, and the remaining output ports of the plurality of output ports are multiple connection output ports for use where two or more coaxial microwave energy supply cables and microwave applicators are connected to two or more multiple connection output ports of the power splitter circuit. The single connection output port is impedance matched and tuned to provide efficient energy transfer when using a single applicator and the multiple connection outlet ports are impedance matched and tuned to provide efficient energy transfer when using a number of applicators anywhere from two to the total number of multiple connection output ports provided. In this way, if a single applicator is used, it is connected to the single connection output port. If multiple applicators are used, each of the multiple applicators is connected to a different multiple connection output port and nothing is connected to the single output port.

Means can be provided to detect whether or not there is an antenna connected to a particular microwave power output port, and whether such antenna is connected to a correct port. This can be done if thermistor or other resistive temperature sensors are used in the applicators, as previously described, and the substantially dc temperature sensor signals are transmitted to the system controller through the coaxial power supply cable. In such instance, the system controller can detect which of the output ports have applicators attached by detecting whether temperature sensors signals are present at such output ports. By detecting the number of applicators attached to output ports of a power splitter circuit and to which of the output ports they are attached, the system controller can determine if a single applicator is connected, and if so, whether it is properly connected to the single connection output port, or whether two or more applicators are connected, and if so, whether they are all properly connected to multiple connection output ports. The system controller can provide an alarm signal if one of multiple applicators is attached to the single connection output port or if a single applicator is connected to one of the multiple output ports.

Further, when using multiple fluid cooled applicators in which cooling fluid is circulated through the applicators and, in embodiments in which fluid is injected into tissue surrounding a portion of the applicators from the fluid cooling system or when fluid is injected directly into the tissue from the applicators without a cooling fluid circulation system, it is necessary to provide a source of cooling fluid and a return line for cooling fluid for each of the applicators, or merely a source fluid for injection into the applicators for injection into the tissue. In order to make connection of a variable number of applicators quick and easy, the invention can provide a cooling fluid circulation system adapted to connect to and provide cooling fluid circulation for a single applicator up to a preset number of multiple applicators. Such a cooling fluid circulation system or an injection fluid supply system of the invention includes a plurality of cooling fluid supply connectors each adapted to be connected to an individual applicator cooling fluid inlet and, if return of cooling fluid is contemplated, an equal plurality of cooling fluid return connectors each adapted to be connected to an individual applicator cooling fluid outlet. Each of the plurality of cooling fluid supply connectors includes a normally closed shut off valve which opens when connected to an applicator cooling fluid inlet. This shut off valve prevents flow of fluid from the cooling fluid supply connector except when connected to a cooling fluid inlet. Each of the plurality of cooling fluid return connectors, if provided, includes a one way flow valve allowing flow of fluid only into a cooling fluid return connector. This prevents fluid flow out of the system through a cooling fluid return connector, but will allow return fluid to flow into the system through such connector when connected to an applicator cooling fluid outlet.

With this cooling fluid circulation system, when only a single applicator is used, one of the plurality of cooling fluid supply connectors is connected to the cooling fluid inlet of the single applicator and one of the plurality of cooling fluid return connectors is connected to the cooling fluid outlet of the single applicator. This will provide flow of cooling fluid through the single applicator. No cooling fluid will flow through any of the cooling fluid supply connectors or the cooling fluid return connectors that are not connected to the applicator. When a plurality of applicators is used, one of the plurality of cooling fluid supply connectors is connected to the cooling fluid inlet of one of the plurality of applicators, and one of the plurality of cooling fluid return connectors is connected to the cooling fluid outlet of one of the plurality of applicators. This will provide a cooling fluid supply connector connected to each of the applicator cooling fluid inlets and a cooling fluid return connector connected to each of the applicator cooling fluid outlets and thereby provide a flow of cooling fluid through each of the plurality of applicators attached to the system. Any number of applicators up to the number of cooling fluid supply connectors in the fluid supply system can be connected to the fluid supply system. Again, no cooling fluid will flow through any of the cooling fluid supply connectors or the cooling fluid return connectors that are not connected to the applicator.

One embodiment of cooling fluid circulation system can also include a cooling fluid reservoir, a pump connected to pump cooling fluid from the cooling fluid reservoir to the plurality of cooling fluid supply connectors, and a fluid conduit connecting the plurality of cooling fluid return connectors to the cooling fluid reservoir to allow flow of fluid from the cooling fluid return connectors to the fluid reservoir. The fluid reservoir may conveniently take the form of a standard IV bag filled with sterile saline solution. Fluid pressure and/or fluid flow sensors may be provided in the cooling fluid circulation system to sense fluid pressure and/or fluid flow to each of the applicators and provide feedback to a pump controller to control the fluid pressure and/or fluid flow to the applicators.

The design of a narrow separation gap between the conductive applicator insertion tip and the insertion end of the conductive outer sleeve provides a zone of high microwave intensity at the gap which can be used to coagulate tissues along the insertion track if the microwave power is applied as the microwave antenna is withdrawn from the treated tissue. This provides coagulation of tissue and blood vessels that may be along the insertion track as well as any disease tissue that may be along the track as the applicator is removed from the tissue. By providing regularly spaced depth markings on the elongate applicator and withdrawing the applicator from the living body in coordination with regular cadence sounds, a substantially constant rate of removal of the applicator from a living body can be achieved for effective track ablation. In addition to the regularly spaced depth markings, it has been found advantageous to also provide a warning marking visible on the outside of the elongate applicator body at a position a known distance toward the attachment end of the applicator from the portion of the applicator that creates the tissue ablation (heating zone or zone of ablation). As the applicator is withdrawn from the treated tissue, appearance of this warning marking indicates when the zone of track ablation or coagulation is getting close to the outer skin surface so that withdrawal of the applicator can be stopped at a desired position short of the skin area to avoid damaging or coagulating tissue in the skin area. Further, the fluid injection system can be controlled to stop fluid injection during this track ablation.

THE DRAWINGS

Other features of the invention will become more readily apparent from the following detailed description when read in conjunction with the drawings in which the accompanying drawings show the best modes currently contemplated for carrying out the invention, and wherein.

DETAILED DESCRIPTION OF THE ILLUSTRATED EMBODIMENTS

Figure 1:
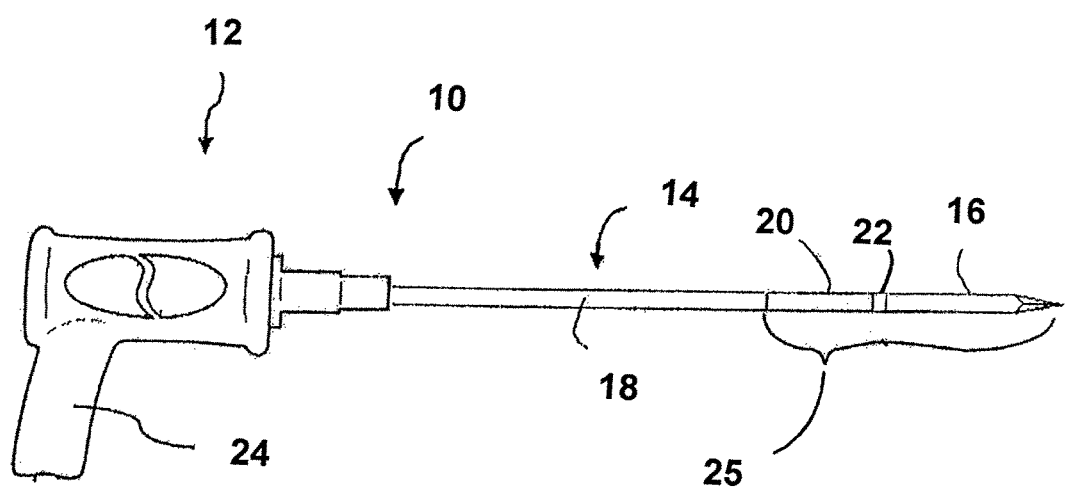
FIG. 1 is a side elevation of an applicator, in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

One embodiment of a microwave applicator of the invention for microwave coagulation and ablation treatment of diseased tissue within living body tissue is illustrated in FIG. 1. The applicator, referred to generally as 10, includes a handle 12 from which a substantially rigid elongate applicator body 14 extends with an insertion tip 16 forming the insertion end portion of the applicator for insertion into a tissue region of the living body. The substantially rigid elongate applicator body 14 includes an outer conductive sleeve 18 extending from the handle 12, a conductive shunt 20, the conductive insertion tip 16, and a dielectric collar 22 positioned between the insertion tip 16 and the shunt 20. As can be seen, dielectric collar 22 joins the conductive insertion tip 16 to both shunt 20 and through shunt 20 to outer conductive sleeve 18. The outside diameters of the exposed portions of the outer conductive sleeve 18, the conductive shunt 20, the dielectric collar 22, and the insertion tip 16 (which may be sharpened at its insertion end 17), are all about equal so as to form a smooth continuous elongate applicator body for insertion into the living body tissue. The elongate applicator body may be coated with a stick resistant dielectric material such as Teflon, not shown. A pistol grip 24 allows the handle to be easily held for manipulation of the applicator.

The applicator has a microwave antenna portion 25 toward the insertion tip of the elongate applicator body 14 to radiate microwave energy from the antenna portion into the living body tissue. Microwave energy is transmitted from the handle 12 through the elongate applicator body to the antenna portion by a coaxial microwave transmission line 26, FIGS. 2-4, within the elongate applicator body and having an inner conductor 29 and an outer conductor 27 separated by a dielectric material 28 positioned therebetween. Although not required, the coaxial transmission line 26 may be a semirigid coaxial cable with copper inner and outer conductors and a Teflon or Teflon and air dielectric material. No outer dielectric insulating material is used. Such coaxial cable will usually have about a fifty ohm impedance which provides a good impedance match to the microwave generator and to typical living body tissue characteristics.

The outer diameter of the coaxial transmission line (also the outer diameter of the outer conductor 27 of the coaxial transmission line) is smaller than the inside diameter of the outer conductive sleeve 18 so a space 82 is provided between the transmission line and the outer conductive sleeve. This space will be referred to as a cooling fluid space. Conductive shunt 20 is positioned around and in electrical contact with both the insertion end portion 83 of the transmission line outer conductor 27, and the outer conductive sleeve 18. Shunt 20 includes a reduced outer diameter end portion 84 toward the handle end of the applicator dimensioned to fit into the space 82 between the outside surface of the outer conductor 27 of the coaxial transmission line 26 and the inside surface of the outer conductive sleeve 18. Shunt 20 can be soldered to both the outer conductor 27 and the outer sleeve 18 to ensure good electrical connection. Soldering will also secure shunt 20 to outer sleeve 18 for a strong connection of shunt 20 to sleeve 18. However, shunt 20 can be secured to sleeve 18 and, if desired, to outer conductor 27, by a bonding agent, such as an epoxy adhesive material. If the bonding agent is conductive, it can replace soldering. With this connection, shunt 20 closes or blocks cooling fluid space 82 toward the insertion end 85 of the outer conductive sleeve 18.

Shunt 20 extends beyond the actual end 86 of the outer conductor to form an enlarged inside diameter shunt portion 87. The insertion end of enlarged diameter shunt portion 87 can accept a reduced diameter mounting portion 88 of the applicator tip 16 with dielectric collar 22 thereon. Dielectric collar 22 fits over the reduced diameter mounting portion 88 of the applicator tip 16, and itself has a reduced diameter insertion portion 89 that fits into enlarged inside diameter shunt portion 87. This interfitting arrangement produces a strong connection of the tip to the remainder of the applicator, with the dielectric collar 22 being bonded to the tip and the shunt by an adhesive material such as epoxy.

Dielectric collar 22, being positioned between shunt 20 and tip 16, electrically insulates tip 16 from shunt 20 and from outer conductive sleeve 18. Since shunt 20 is electrically connected to the outer conductor 27 of the coaxial transmission line 26, shunt 20 becomes an extension of the outer conductor 27 and the insertion end 90 of the conductive shunt 20 becomes the effective insertion end of the outer conductor 27. The inner conductor 29 of the coaxial transmission line extends toward the insertion end of the applicator beyond the insertion end 91 of the coaxial transmission line dielectric material 28 to an inner conductor insertion end 92. However, both the insertion end 91 of the coaxial transmission line dielectric material and the insertion end 92 of the coaxial transmission line inner conductor are within the enlarged inside diameter shunt portion 87 of shunt 20 and do not extend beyond the insertion end 90 of shunt 20.

The reduced diameter mounting portion 88 of applicator tip 16 also includes a tip tab 93 extending therefrom toward the handle end of the applicator and the insertion end 91 of the coaxial transmission line dielectric 28. The tip tab 93 is positioned so that the extension of the coaxial transmission line inner conductor 29 beyond the end 91 of the coaxial transmission line dielectric 28 is adjacent to and can be secured in electrical contact, such as by soldering, to the tip tab 93. With this arrangement, inner conductor 29 does not extend into tip 16, but is merely adjacent to and electrically connected to tip tab 93.

Figure 10:
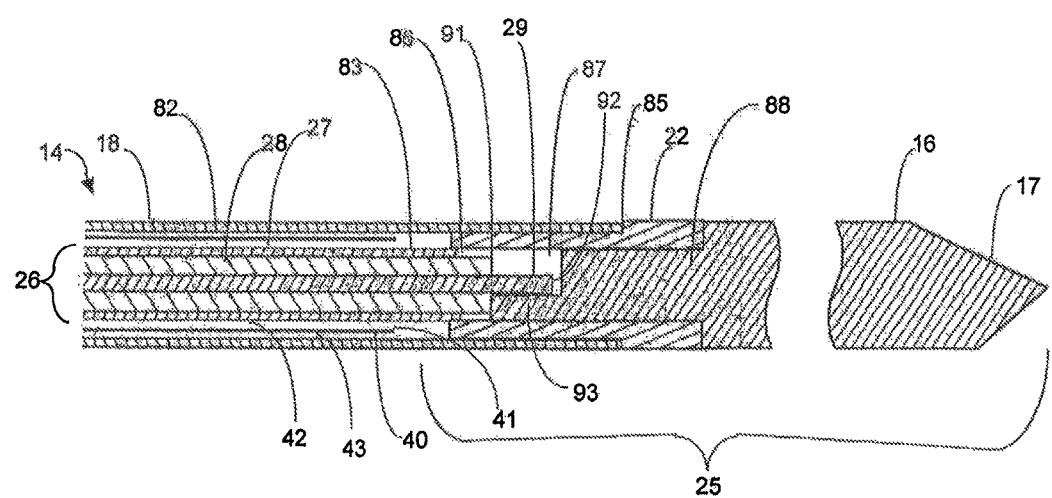
FIG. 10 is a vertical section similar to that of FIG. 2 of a different embodiment of applicator of the invention.

As constructed, the conductive outer sleeve 18 may be of a metal material such as stainless steel, the conductive tip and the shunt may be formed of a metal material such as brass or stainless steel, and the dielectric insulating collar may be formed of a substantially rigid plastic material. All such parts may be bonded using an epoxy adhesive. Further, while the construction described for this illustrated embodiment provides an embodiment of a microwave antenna toward the insertion end of the applicator, various other applicator constructions can be used to form a microwave antenna toward the insertion end of the applicator and to form an insertion end of the applicator. For example, FIG. 10 shows an alternate embodiment of the insertion portion of the applicator where the shunt is not used. As shown in FIG. 10, the conductive applicator insertion tip 16 is connected directly to the outer conductive sleeve 18 by dielectric collar 22 which electrically insulates the conductive applicator insertion tip from the conductive outer sleeve 18. Also, the end of dielectric collar 22 toward the attachment end of the applicator extends into the space 82 between the outer conductive sleeve 18 and the outer conductor 27 of the coaxial microwave transmission line 26 to electrically insulate the outer conductive sleeve 18 from the outer conductor 27. In this embodiment, the outer conductive sleeve 18 is not electrically connected to the outer conductor 27. Dielectric collar 22 also forms the end toward the insertion end of the applicator of the cooling fluid space 82. Similarly to the construction shown in FIG. 2, the insertion tip 16 includes tip tab 93 which is coupled to the inner conductor 29. This construction of the antenna and insertion end of the applicator has also been found satisfactory for use in the invention.

Figure 4:
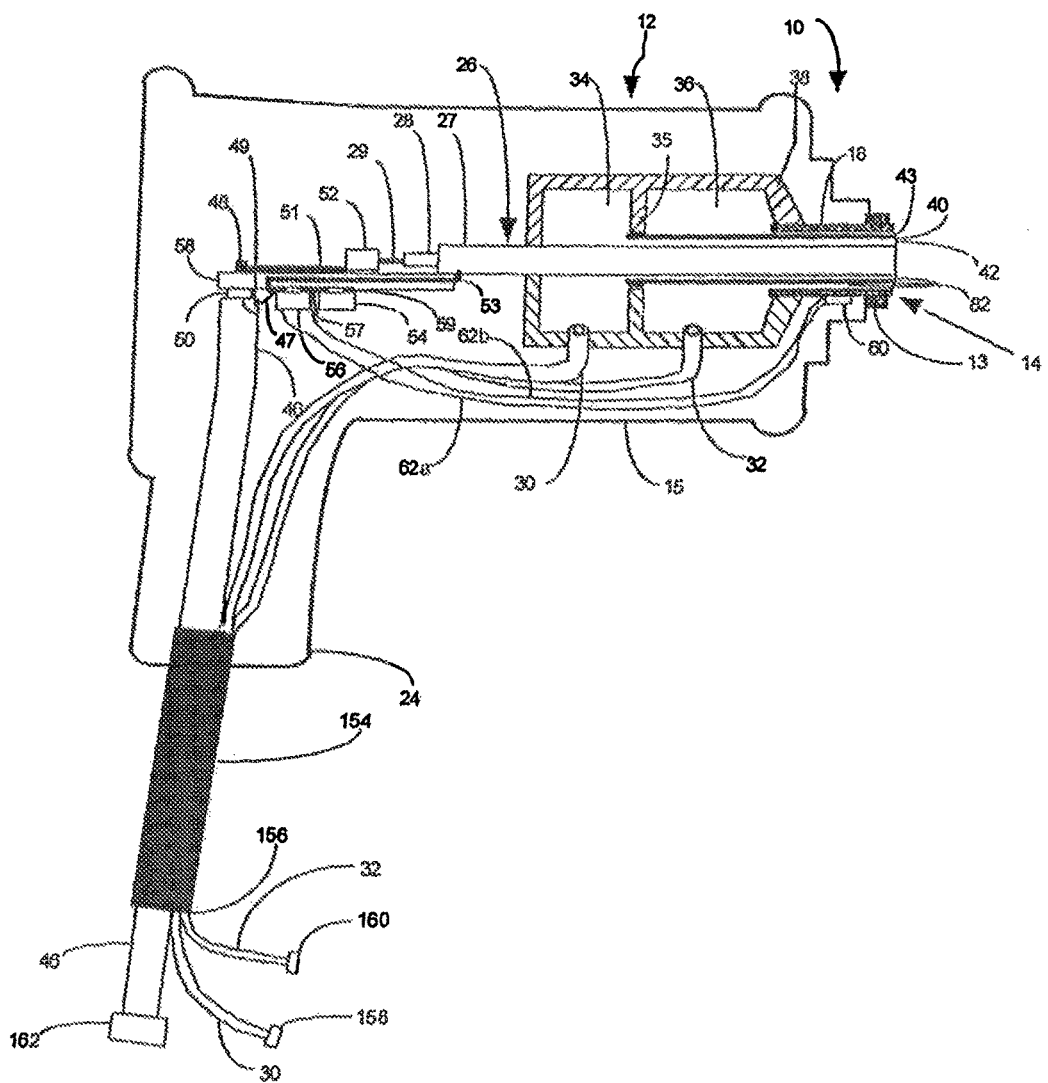
FIG. 4 is a vertical sectional of the handle portion of the applicator of FIG. 1.

As shown in FIG. 1, elongate applicator body 14 extends from handle 12. As shown in FIG. 4, outer conductive sleeve 18 is secured in the forward portion 13 of handle body 15 and in the forward end of cooling fluid reservoir 38, which cooling fluid reservoir 38 is mounted within handle body 15. Cooling fluid reservoir 38 includes two reservoir chambers 34 and 36 separated by guide sleeve 40 that extends from connection to reservoir partition 35 into outer conductive sleeve 18 and within outer conductive sleeve 18 toward the insertion end of the applicator. The guide sleeve 40 may be a thin walled plastic sleeve made of polyimide plastic such as Kapton. Attachment of the outer conductive sleeve 18 to handle body 15 and fluid reservoir 38, and attachment of guide sleeve 40 to reservoir partition 35, may be with glue, epoxy, or other bonding agent. Coaxial transmission line 26 extends through cooling fluid reservoir 38 and into guide sleeve 40. Coaxial transmission line 26 extends through the entire length of guide sleeve 40 and beyond the guide sleeve insertion end 41, FIG. 2, and into shunt 20.

Figure 2:
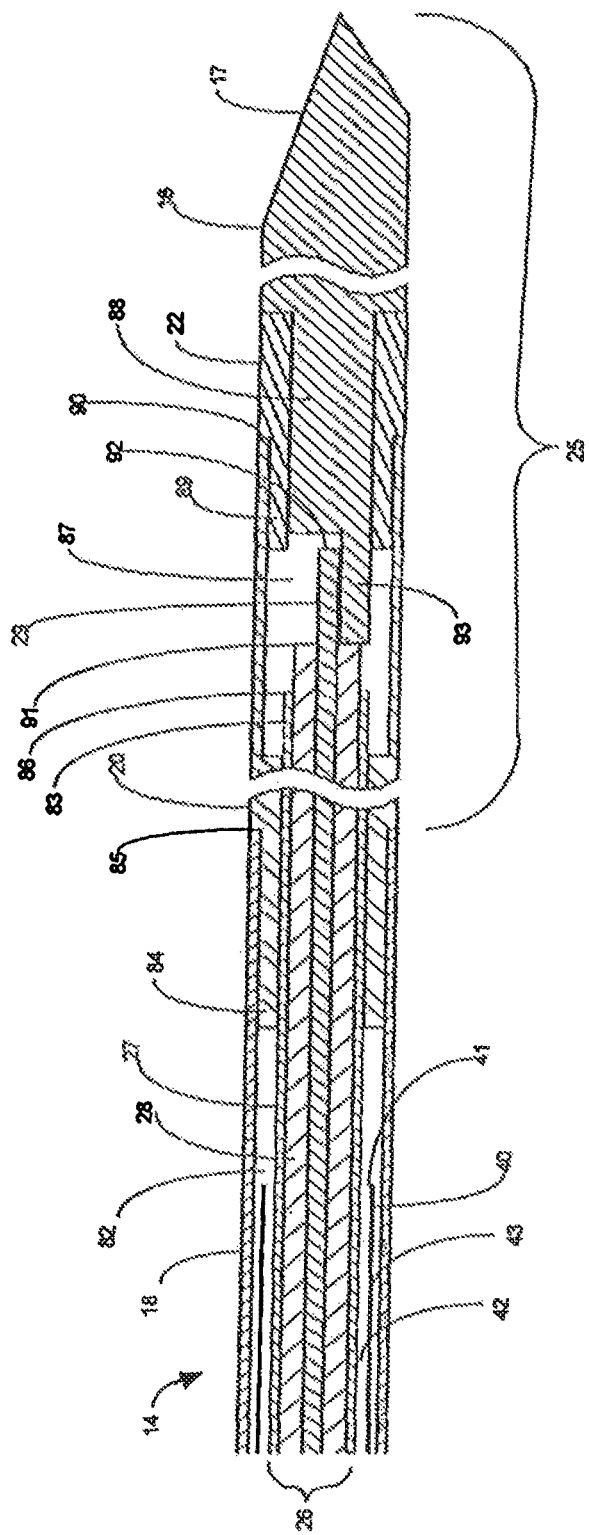
FIG. 2 is a vertical section of a portion of the applicator of FIG. 1.
Figure 3:
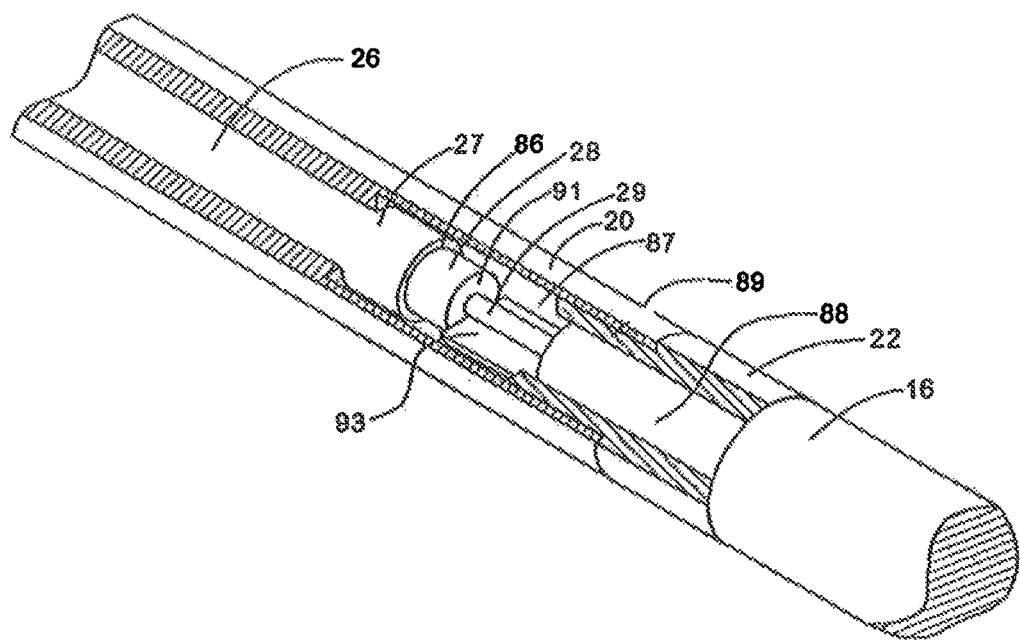
FIG. 3 is a cut away perspective view of a portion of the applicator of FIG. 2.

As seen in FIGS. 2 and 4, guide sleeve 40 extends into cooling fluid space 82 between the outside of coaxial transmission line 26 and the inside of outer conductive sleeve 18. Guide sleeve 40 divides cooling fluid space 82 into an inner cooling fluid space 42 and an outer cooling fluid space 43 along the length of guide sleeve 40 in space 82. Inner cooling fluid space 42 is formed between the outside surface of coaxial transmission line 26 and the inside surface of guide sleeve 40 and outer cooling fluid space 43 is formed between the outside surface of guide sleeve 40 and the inside surface of outer conductive sleeve 18. Reservoir chamber 34 communicates with inner cooling fluid space 42 and reservoir chamber 36 communicates with outer cooling fluid space 43.

While either reservoir chamber 34 or 36 could be a cooling fluid inlet or cooling fluid outlet, it has been found for ease of placement of the temperature sensor, as will be explained in respect of the location of temperature sensor 60, that reservoir chamber 34 can be the cooling fluid inlet reservoir and reservoir chamber 36 can be the cooling fluid outlet reservoir. In such instance, cooling fluid to the applicator will flow from a source of cooling fluid, not shown, through tubing 30 into reservoir chamber 34. From reservoir chamber 34, cooling fluid flows through inner cooling fluid space 42 along the outside surface of coaxial transmission line 26 to cool the outside surface of coaxial transmission line 26. As previously indicated in regard to FIG. 2, cooling fluid space 82 into which guide sleeve 40 extends is blocked at the insertion end portion of outer conductive sleeve 18 by the reduced diameter portion 84 of shunt 20 which fits into and blocks the insertion end of space 82. As seen in FIG. 2, the insertion end 41 of guide sleeve 40 ends before reaching the end of space 82 created by shunt 20 so as to leave an undivided fluid space portion which connects the inner cooling fluid space 42 and the outer cooling fluid space 43. Thus, as cooling fluid flowing in inner cooling fluid space 42 toward the insertion end of the applicator reaches the insertion end 41 of guide sleeve 40, it flows into the undivided space 82 around the insertion end 41 of guide sleeve 40 into outer cooling fluid space 43 and flows along the inside surface of outer conductive sleeve 18 back into reservoir chamber 36 and out fluid outlet tube 32 back to the fluid supply to be cooled and recirculated or to a fluid drain.

Figure 5:
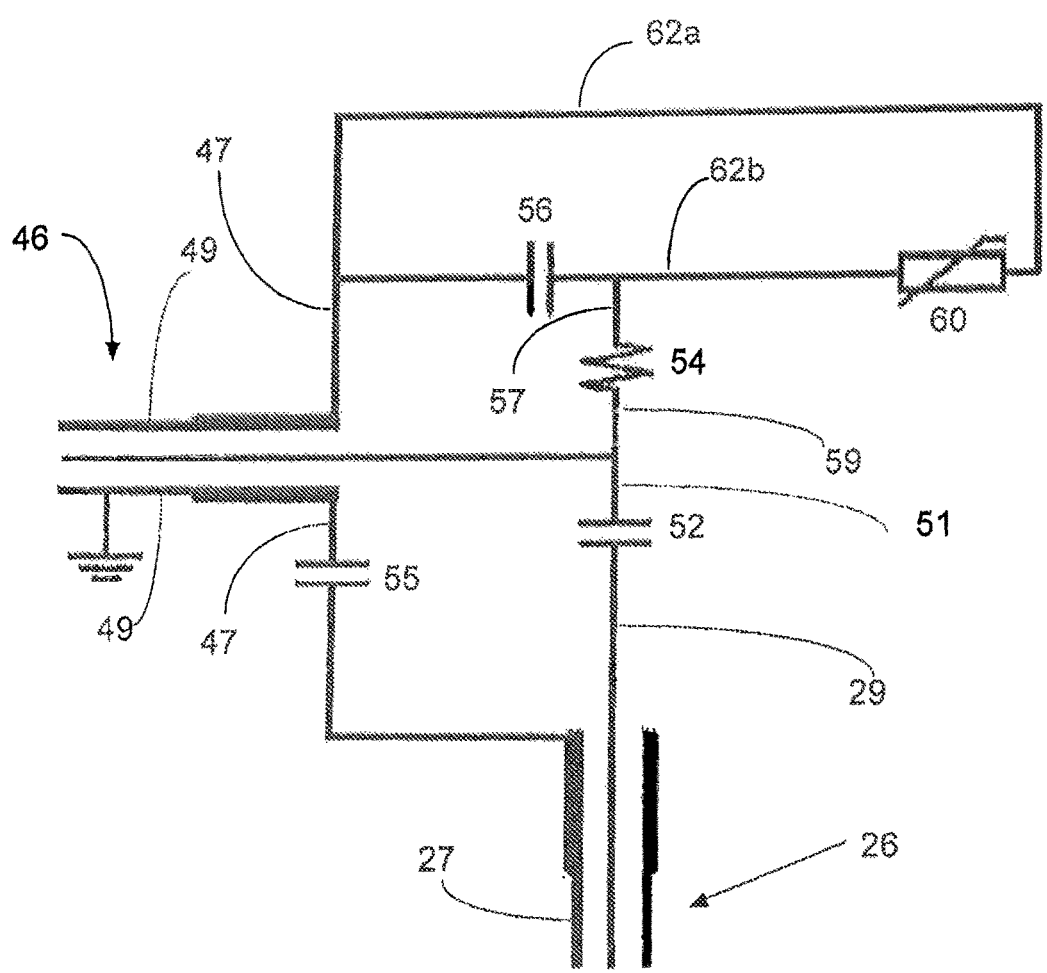
FIG. 5 is a circuit diagram of the electrical connections within the handle portion of the applicator as shown in FIG. 4.

As shown in FIG. 4, microwave energy is provided to the applicator from a microwave generator, not shown, by a coaxial microwave energy supply cable 46 that provides a path for the microwave energy from the generator to the applicator. The coaxial microwave energy supply cable 46 is typically a flexible fifty ohm coaxial cable containing an inner or center conductor 48, an outer conductor 49, and a dielectric spacer 50 therebetween. In the illustrated embodiment, the connection between the flexible coaxial microwave energy supply cable 46 and the semi-rigid coaxial transmission line 26 is provided through a coupling circuit on a printed circuit card 58 which supports small chip capacitors and a resistor, (see also FIG. 5 which is a circuit diagram of the circuitry of FIG. 4). The coaxial microwave energy supply cable center conductor 48 is connected by conductive metal path 51 on the circuit card 58 to capacitor 52 which is connected to inner conductor 29 of coaxial transmission line 26. The coaxial microwave energy supply cable outer conductor 49 is connected by conductive element or wire 47 to conductive metal path 53 on the circuit card 58 which is connected to outer conductor 27 of coaxial transmission line 26. This provides a direct path for the microwave currents to flow between the outer conductors. Circuit diagram FIG. 5 shows a capacitor 55 connected between the two outer conductors 49 and 27 which is not necessary and not shown in FIG. 4, but may be advantageous to include to provide further isolation of the microwave antenna from dc currents in the flexible coaxial microwave energy supply cable 46.

A temperature sensor in the form of a thermistor 60 is placed over the outer conductive sleeve 18 and bonded to it so that it is approximately the same temperature as the outer conductive sleeve 18. Thermistor 60, when placed at the location shown in FIG. 4, measures the temperature of outer conductive sleeve 18 at about its handle end, which will be at approximately the temperature of the cooling fluid after flowing through the elongate applicator body 14. Thermistor 60 can be located at other locations that enable it to indicate the approximate temperature of the cooling fluid after or during flow through the applicator. When located as shown, thermistor 60 measures the approximate temperature of the cooling fluid between guide sleeve 40 and the outer conductive sleeve 18 as the cooling fluid returns to the cooling fluid outlet reservoir chamber 36 after flowing through inner and outer cooling fluid spaces 42 and 43. The cooling fluid at this location will have reached approximately its highest temperature. Thermistor 60 could be located in the cooling fluid itself, if desired, such as in cooling fluid outlet reservoir chamber 36. The function of this thermistor 60 is to provide an indication that the cooling fluid is actually flowing inside the applicator whenever the microwave power is applied. During the application of microwave energy, the microwave energy causes self heating of the coaxial transmission line 26 in the applicator. This increases the temperature of coaxial transmission line 26 thereby heating the surrounding parts between thermistor 60 and coaxial transmission line 26. Without circulation of cooling fluid, applicator outer conductive sleeve 18 can reach temperatures that can damage normal tissue. The flow of cooling fluid inside the applicator along coaxial transmission line 26 and outer conductive sleeve 18 removes much of that generated heat so that thermistor 60 remain cooler when the cooling fluid is flowing than if there is no fluid flow. If fluid flow stops or is restricted, the fluid will heat to a higher temperature than when properly flowing. When properly flowing, the applicator outer conductive sleeve 18 will remain below tissue damaging temperatures.

A thermistor is a resistive electrical device that varies its resistance depending upon its temperature. The two wires 62a and 62b from thermistor 60 are connected across capacitor 56. Wire 62a connects to capacitor 56 and also connects directly to outer conductor 49 of the flexible coaxial cable 46. Wire 62b attaches to the opposite side of capacitor 56 and also to one side of resistor 54 through conductive metal path 57. The other side of resistor 54 connects to conductive metal path 51 via a wire or conductive metal path 59. Thus, thermistor 60 is connected electrically between inner conductor 48 and outer conductor 49 of flexible coaxial cable 46. This enables the resistance of the thermistor 60 to be monitored by a direct electrical current that is passed from the center conductor 48 through conductive metal traces 51 and 59 to resistor 54 and conductive metal trace 57 and wire 62b to thermistor 60 and back via wire 62a and wire 47 to the outer conductor 49 of flexible coaxial cable 46. Capacitor 52 prevents the direct electrical current from flowing into inner conductor 29 of coaxial transmission line 26 and therefore prevents the direct electrical current from flowing into the applicator antenna and living body into which the applicator is inserted. If capacitor 55 is provided in the circuit, it prevents the direct electrical current from flowing into the outer conductor 27 of coaxial transmission line 26 to further ensure that direct electrical current does not flow into the antenna and into the living body into which the applicator is inserted. This described circuitry allows the flexible coaxial microwave energy supply cable to serve a dual purpose. The dc current for monitoring of the resistance of thermistor 60 passes through the flexible coaxial microwave energy supply cable 46 along with the microwave energy that flows through the flexible coaxial microwave energy supply cable 46 from the microwave energy generator to the applicator. With the arrangement described, the temperature indicating signal is carried between the thermistor and the system controller over the same two coaxial cable conductors 48 and 49 that carry the microwave power from the microwave generator to the applicator. This eliminates the need for separate additional wires from the handle to the system controller to carry the temperature signals from the thermistor.

As indicated, the signal from the thermistor 60 provides an indication to the system controller of the temperature of the outer conductive sleeve and the cooling fluid circulating in the applicator. With the microwave power applied to the applicator, which results in heating of coaxial transmission line 26, as long as cooling fluid is properly flowing in the applicator, the temperature of thermistor 60 will remain low. If the cooling fluid stops flowing in the applicator or flow is restricted for some reason, the coaxial transmission line 26 will begin to heat and the temperature of outer conductive sleeve 18 and of any non-flowing or slowly flowing fluid in the applicator will also increase. This increases the temperature of thermistor 60. This increase in measured temperature of thermistor 60 provides an indication that cooling fluid is not flowing properly and the system controller can activate an alarm or activate other corrective action.

Figure 6:
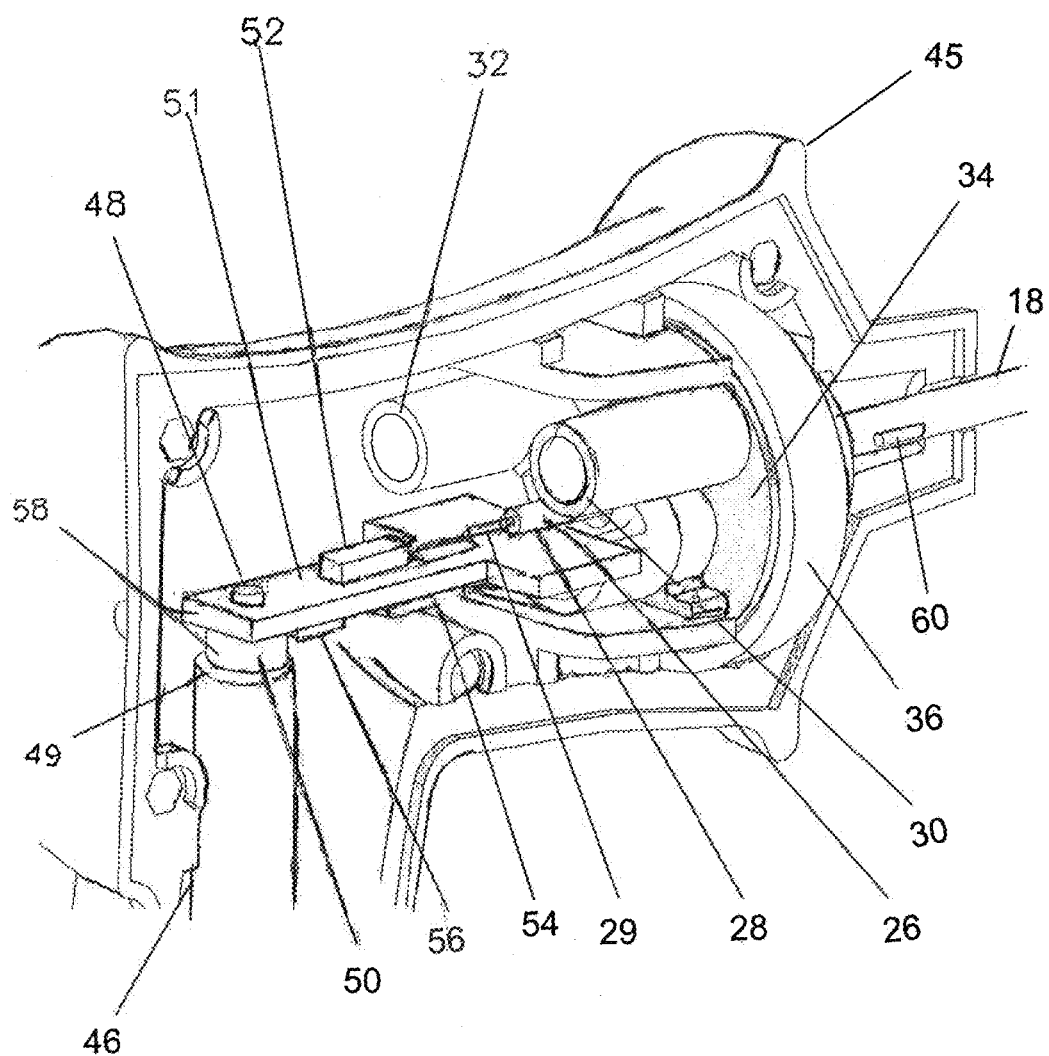
FIG. 6 is a perspective cut away view of another embodiment of handle for the applicator of the invention.

FIG. 6 shows a cut away perspective view of a handle similar to that of FIG. 4, but with a slightly different configuration of handle body 45 and different orientation of inlet 30 and outlet 32 tubes from reservoir chambers 34 and 36. However, the configuration of the handle components is substantially the same and components are numbered the same as in FIG. 4. The wires from the thermistor 60 are not shown. FIG. 6 gives a better illustration of the actual construction of the applicator handle.

As can be appreciated from the above explanation, in addition to providing a means by which the applicator can be held and manipulated for insertion into the living body, handle 12 serves as an interface between the substantial rigid elongate applicator body 14 and the flexible coaxial microwave energy supply cable extending from the microwave generator to the applicator, provides for the insertion of the temperature signals onto the flexible coaxial microwave energy supply cable, and serves as an interface between the flexible fluid hoses from and to a source of cooling fluid and the cooling fluid reservoirs. Various configurations of handles can be used. While the flexible coaxial microwave energy supply cable and the flexible fluid hoses are shown extending from the end of the handle grip (and could be enclosed in a sheath, if desired), connectors could be provided directly on the handle so that the flexible coaxial microwave energy supply cable could be connected to and disconnected from the handle and so that the flexible fluid hoses could also be connected to and disconnected from the handle. In the embodiment shown in FIG. 4, the flexible coaxial microwave energy supply cable 46 and the flexible fluid hoses 30 and 32 are shown coming together in side-by-side relationship in the handle 12 and entering a sheath 154 which extends out of the end of the pistol grip 24 to keep the cable and hoses together for a distance extending from the handle. This allows easier maneuvering of the applicator during use. The hoses 30 and 32 and cable 46 extend from the end 156 of the sheath 154 and the hoses terminate in hose connectors 158 and 160 adapted for connection to a cooling fluid supply hose connector and a cooling fluid return hose connector. Coaxial cable 46 terminates in a cable connector 162 adapted to connect to a further microwave energy supply cable. Various materials can be used for the sheath 154. A plastic braid material that functions like the old "Chinese Handcuff" to tighten around the enclosed cable and hoses has been found satisfactory to provide a good outer covering to improve the handling and storage of the applicator, and to allow heat generated by the coaxial cable to easily pass through it.

Figure 7:
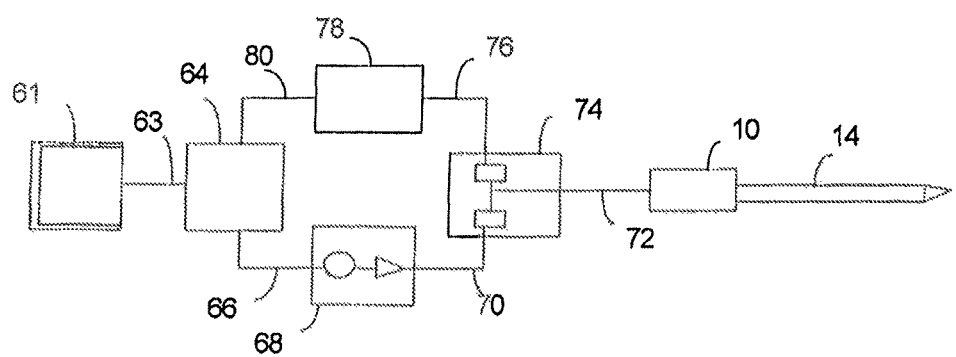
FIG. 7 is a block diagram of a system for microwave therapy using the applicator of the invention.

FIG. 7 is a functional block diagram of a basic system of the invention as described above using a single applicator for patient treatment. An operator interface 61, such as a computer screen and keyboard or a simple touch screen, is provided for display and monitoring of the system controls and the treatment procedures. The user interface is connected to a system controller 64, such as a computer processor, by a cable 63. The controller provides control and monitoring to a microwave generator 68 through a cable 66. The generator 68 has a microwave oscillator where the power amplitude can be controlled and monitored by the controller 64 including the measurement of both the forward and reflected power at the output of the generator 68. The generated microwave power is then directed to a multiplexer and power splitter circuit 74 by a transmission line cable 70, such as a coaxial cable. The microwave path inside the multiplexer and power splitter circuit 74 contains an impedance matched microwave path directing the microwave power to the applicator 10 with elongate applicator body 14 by a flexible coaxial microwave energy supply cable 72. As described, within the applicator 10 there is a dc current path that flows through a temperature sensing thermistor that enables a direct current to also flow through the coaxial microwave energy supply cable 72. This direct current that is used to measure the temperature within the applicator elongate body 14 is separated from the microwave power signal in the multiplexer portion of the multiplexer and power splitter circuit 74 and is sent along a dc circuit path 76 that is directed to a temperature monitoring circuit 78. The temperature monitoring circuit 78 then directs a temperature signal back to the controller 64 through a cable 80 to enable the controller to monitor and control microwave power levels generated by microwave generator 68 to limit the microwave power transmitted to the applicator if excessive temperatures are measured in the applicator 10. Temperature monitoring circuit 78 may be part of the controller 64.

In many instances, it will be desired to provide patient treatment using a phased array of applicators rather than a single applicator. When using a phased array, a plurality of applicators are inserted into the patient in approximately parallel orientation in a pattern approximately evenly spaced apart along the circumference of an insertion circle around the tissue to be treated. Each applicator should be inserted so that the radiating antenna is at approximately the same depth position with respect to the tissue to be treated so as to have the radiation feedpoints approximately aligned side by side. The use of multiple applicators in phased arrays generally allows better control of the applicators to produce better uniformity of power deposition, temperature, and/or coagulation of tissue throughout a tumor volume to be treated and particularly at the tumor margins than when using a single applicator. The use of phased arrays can also reduce microwave heating along the shafts of the applicators due to cross coupling of the energy between the antennas that are driven in phase and separated by a distance that provides for partial power cancellation along the outer portion of the inserted applicators and an increase in tissue heating between these inserted applicators. With phased arrays, pretreatment planning can be used to provide an ideal insertion pattern and power and phase application to the array of applicators to produce and control the desired heating. The treatment is thereby optimized and controlled by the aid of a numerical calculation of either the planned insertion pattern and number of antennas or the actual pattern achieved as indicated by various non-invasive imaging processes such as computer tomography (CT), ultrasound, or magnetic resonance imaging (MRI). Power amplitude and phase of each of the inserted applicators can be adjusted as directed by a computer-controlled system using the predicted power patterns from the computer numerical model. Further, actual temperature measurements can be taken and compared with the predicted power patterns and predicted temperatures and the system controlled to compensate for differences.

In a phased array embodiment of the invention, a single microwave generator is used to provide the microwave power for all applicators. The generator will usually operate at 915 MHz, which is an emission frequency commonly licensed for medical applications. This single generator is connected to a passive, non-switching, microwave impedance matched power splitter (divider) which is used to direct power simultaneously to multiple ports that are connected to one or more microwave dipole antenna such as described for the above described applicators. This arrangement provides approximately equal power simultaneously to each of the output connection ports. This arrangement also provides equal phase output of the microwave energy at each of the output ports. Thus, when multiple antennas are connected to the ports of the power splitter, they have equal power and equal relative phase and are thus correctly called a phased array of antennas. The cables going to the radiating points on each antenna are maintained at the same electrical length so that the radiated energy from the antennas are phase synchronous and phase coherent. Phase synchronous meaning that there is a fixed phase relationship between the radiation phase of all antennas and phase coherent meaning that the relative radiated phase from each antenna is approximately the same. Since different array patterns are desirable for different optimized treatments, and desired treatments can use a single applicator or varying numbers of multiple applicators, it is desirable to have a system which can power and monitor a single applicator or a multiple number of applicators. However, present systems are usually designed to optimize power delivery to either a single applicator or to a set number of multiple applicators. This does not provide the flexibility desired to configure different arrays using a single delivery system. It would also be desirable in array power systems to have an indication as to whether or not there is an antenna connected to a particular microwave power output port and an indication as to whether antennas are correctly connected.

Figure 8:
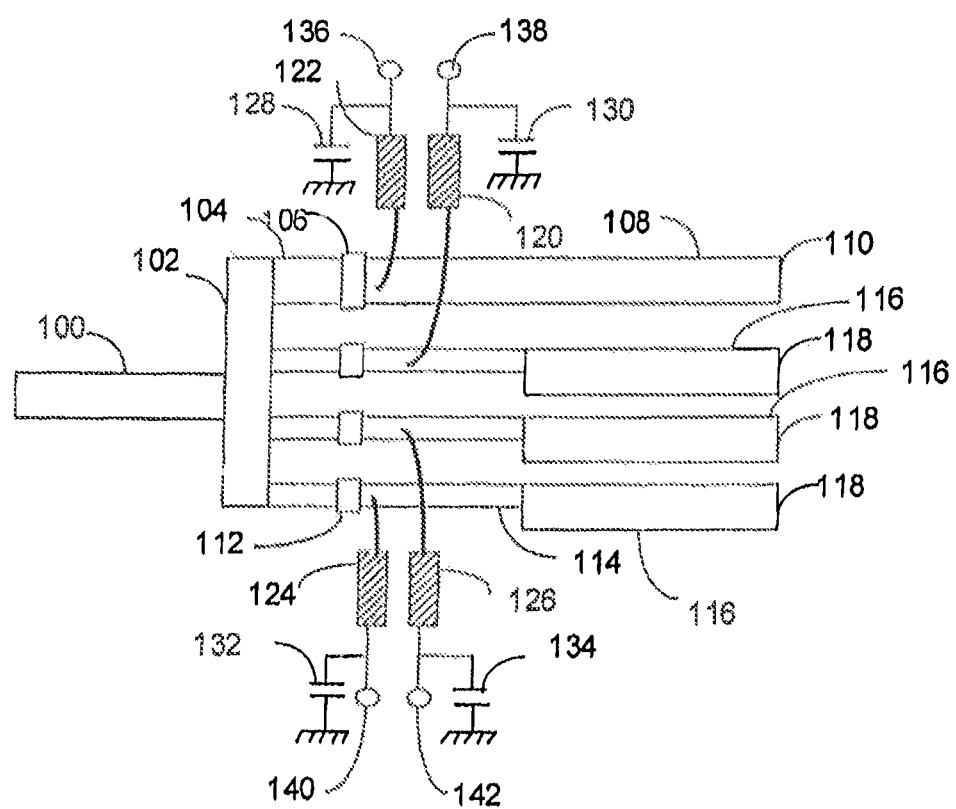
FIG. 8 is a block diagram of a system of the invention for microwave therapy using an array of applicators of the invention.

FIG. 8 shows an embodiment of a multiplexer and power splitter circuit according to the invention that provides for the separation of temperature signals from microwave power signals for a plurality of applicators and which can provide optimization for attachment of a single applicator, two applicators, or three applicators. Microwave power signals from a microwave generator, not shown, are supplied to the multiplexer and power splitter circuit through coaxial cable 100, generally of fifty ohm impedance. The multiplexer and power splitter circuit is generally on a printed circuit card made of low loss dielectric material such as Teflon based material with a ground plane on one side and the circuit show in FIG. 8 that represents the conductive paths forming various transmission lines on the other side. The input microwave power signal connects to an input in the form of a conductive patch 102 that provides a power splitting section. This directs microwave power to four paths, one path shown by path 104, and three identical paths shown by paths 114. Along path 104 is a chip type capacitor 106 that conducts microwave power but blocks direct current to prevent direct current from reaching power splitting patch 102. The input microwave power flows through capacitor 106 to circuit output port 110 along transmission line 108. The transmission lines 104 and 108 are fifty ohm transmission lines which together have an electrical length delay of one hundred eighty degrees at the microwave operating frequency. Capacitor 106 has a low impedance of typically less than two ohms reactive impedance to avoid mismatching the transmission line. This then directs microwave power from the input transmission line 100 to the circuit output port 110. Output port 110 forms an output port for connection of a single applicator antenna through a fifty ohm impedance coaxial microwave energy supply cable attached to output port 110. This output port 110 is used if only a single antenna is to be connected to the multiplexer and power splitter circuit, and is sometimes referred to herein as a single connection output port.

Power splitter conductive patch 102 is also connected to three identical other transmission lines having microwave input sections 114 each with a series chip capacitor 112 along the path, and microwave output sections 116. Similarly to capacitor 106, each capacitor 112 in the microwave input section has a low impedance of typically less than two ohms reactive impedance to allow microwave power to pass but block direct current flow to prevent direct current from reaching power splitting patch 102. The overall length of the microwave input section of the transmission lines from the power splitter conductive patch 102 through the capacitor 112 along path 114 is approximately ninety degrees delay at the microwave frequency. Also the characteristic impedance of the microwave input section of the transmission lines 114 with capacitors 112 of typically between seventy and ninety ohms from the power splitter conductive patch 102 to the end of path 114 is used to provide an impedance matching section for the input when two or three applicators are connected to the multiple connection output ports 118. The microwave output sections 116 are fifty ohm sections that connect the lines 114 to the multiple connection output ports 118 and these microwave output sections 116 are typically the length to delay the microwave signal approximately ninety degree. The fifty ohm impedance of the microwave output sections 116 provide impedance matching for the flexible coaxial microwave energy supply cables and the applicators connected to the output ports 118.

The described power splitter circuit forms an impedance matched microwave power splitter that when a single applicator is to be used it alone is connected to the single connection output to port 110. When this is the case the other three output ports, each a multiple connection output port 118, are not connected to an applicator. The path length from the power splitter conductive patch 102 to each of these multiple connection output ports 118 is one hundred eighty degrees. The microwave power that travels to these multiple connection output ports 118 is reflected completely back when there is no connection to the ports and this reflected power is reflected with the same phase angle as the incoming power to these ports because this is an open circuit termination. This means that the overall phase delay of the power from the power splitter conductive patch 102 to the multiple connection output ports 118 and back to the power splitter conductive patch 102 is three-hundred-sixty degrees. This unique phase delay then appears to the power splitter as an open circuit. Thus, the open ports 118 turn these paths into tuning paths that do not reflect power that would reach the input line 100, but would direct the full power only to single connection output port 110 to the single applicator that is connected to output port 110 for efficient power transfer to the single applicator.

When two or three applicators are connected to respective multiple connection output ports 118, there will be no applicator connected to the port 110. The path delay between the power splitter conductive patch 102 and the output port 110 is also one-hundred-eighty degrees. Therefore, the delay to the output port 110 and back to the conductive patch 102 is three-hundred-sixty degrees. When there is no applicator attached to the single connection output port 110 it also turns into a tuning path for the microwave energy. The result is that the microwave multiplexer and power splitter circuit is an impedance matched splitter which automatically allows the power to be directed to the connection of 1, 2, or 3 applicators. It would not be permitted to attach only a single applicator to one of the multiple connection output ports 118 because it would result in an impedance mismatch and would cause unacceptable reflected power to the input line 100. Also, if no applicators are connected to any of the ports of the power splitter circuit, all transmission paths appear as open circuits. This allows multiple power splitter circuits to be use to provide for more than three applicators when desired. For example, if two power splitter circuits are used anywhere between one and six applicators can be connected to the system.

The multiplexer and power splitter circuit also includes an inductive coil or choke 120, 122, 124, and 126 connected to each of the transmission lines 104 and 114. Each of these inductive coils is connected through a capacitance to the ground chassis with capacitors 128, 130, 132, and 134, respectively. These capacitors and the inductive coils filter the microwave signals from the temperature sensing ports 136, 138, 140, and 142, but pass direct current signals from the transmission lines 108 and 114 to these temperature sensing ports. These temperature sensing ports are connected to temperature monitoring circuitry and then to the system computer or controller for detection of the measured resistance of the thermistors that are connected to the two wire coaxial microwave energy supply connectors of the applicators as previously described. These direct current temperature sensing signals from the applicators to the temperature sensing ports provide a measurement to the system controller of the temperature measured by the temperature sensors in each of the applicators.

These direct current temperature sensing signals from the applicators to the temperature sensing ports also provide a measurement to the system controller of whether applicators are connected to particular output ports of the multiplexer and power splitter circuit. If an applicator is connected to a particular multiplexer and power splitter circuit output port, for example to output port 110, a temperature signal will be present on temperature sensing port 136. The system controller will then know that an applicator is connected to output port 110. Similarly, if a temperature signal is present on temperature sensing ports 138 and 142, the system controller will know that two applicators are connected to two of the multiple connection output ports 118 and will be able to identify which of the two output ports have applicators connected thereto. If the system controller senses temperature signals on temperature sensing ports 136 and 138, the system controller knows that there are two applicators connected to the multiplexer and power splitter circuit, but that the applicators are not properly connected since one of the two applicators is improperly connected to single connection output port 110 while the other of the two applicators is properly connected to one of the multiple connection output port 118. The system controller can then provide a warning signal to a system user indicating that the applicators are improperly connected, and that the applicator connected to the single connection output port 110 should be disconnected and connected to one of the multiple connection output ports 118. The use of this special multiplexer and power splitter circuit, in addition to providing an indication that the proper number of applicators are connected to the correct output ports for efficient and desired microwave power delivery to the connected applicators, also enables the measurement of applicator cooling temperature to determine that fluid is properly flowing in each of the connected applicators to protect the normal body tissues.

If temperature sensing is not required, but the sensing of the attachment of microwave applicators to power splitter circuits is desired, the thermistor or other temperature sensors that provide direct current temperature signals can be replaced with regular resistors which will provide substantially dc signals in the manner of thermistor to indicate that microwave applicators are attached to a power splitter output port and indicate to which port or ports the applicators are attached. This use of resistors will be considered equivalents of the thermistors or other temperature sensors that provide direct current temperature sensor signals for the purposes of the applicator detection.

Figure 11:
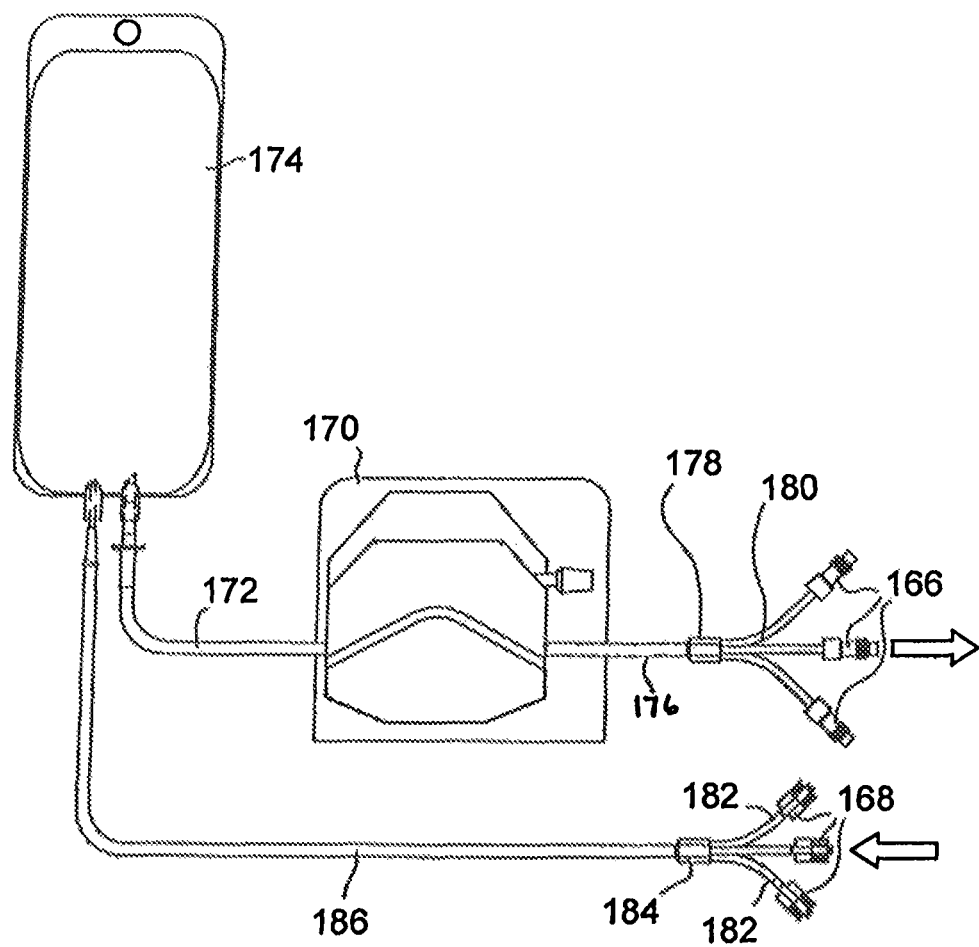
FIG. 11 is a schematic representation of a cooling fluid circulation system of the invention.

Another consideration when using arrays of multiple fluid cooled applicators in which cooling fluid is circulated through the applicators, is the necessity to provide a source of cooling fluid and a return line for cooling fluid for each of the applicators. In order to make connection of a variable number of applicators quick and easy, the invention can provide a cooling fluid circulation system adapted to connect to and provide cooling fluid circulation for a single applicator up to a preset number of multiple applicators. Referring to FIG. 11, a cooling fluid circulation system of the invention includes a plurality of cooling fluid supply connectors 166, (here shown as three connectors) each adapted to be connected to an applicator cooling fluid inlet, such as a cooling fluid inlet connector 158 of FIG. 4. An equal plurality (here three) of cooling fluid return connectors 168 are provided each adapted to be connected to a cooling fluid outlet, such as a cooling fluid outlet connectors 160 of FIG. 4. Each of the plurality of cooling fluid supply connectors 166 includes a normally closed shut off valve which opens when connected to an applicator cooling fluid inlet. This shut off valve prevents flow of fluid from the cooling fluid supply connector except when connected to a cooling fluid inlet. Each of the plurality of cooling fluid return connectors 168 includes a one way flow valve allowing flow of fluid only into a cooling fluid return connector. This prevents fluid flow out of the system through a cooling fluid return connector 168, but will allow return fluid to flow into the system through such connector when connected to an applicator cooling fluid outlet 160. The cooling fluid supply connectors 166 are configured to connect to the cooling fluid inlet connectors 158, but not to the cooling fluid outlet connectors 160. Similarly, the cooling fluid return connectors 168 are configured to connect to the cooling fluid outlet connectors 160, but not to the cooling fluid inlet connectors 158. In this way, a user cannot improperly connect the cooling fluid connections.

In the system of FIG. 11, a cooling fluid pump 170 draws cooling fluid through line 172 from a cooling fluid reservoir 174 and pumps it through line 176 and line splitter 178 into lines 180 to the plurality of cooling fluid supply connectors 166. Each of the cooling fluid return connectors 168 is connected to a line 182 connecting to a line joiner 184 connected through line 186 to the cooling fluid reservoir 174. Thus, cooling fluid is pumped from the reservoir to the plurality of cooling fluid supply connectors 166. Cooling fluid from an applicator is allowed to flow from the cooling fluid return connectors 168 back to the fluid reservoir 174. The fluid reservoir 174 may conveniently take the form of a standard IV bag filled with sterile saline solution. This provides sterile saline solution as the cooling fluid.

With the illustrated cooling fluid circulation system of the invention, when only a single applicator is used, one of the plurality of cooling fluid supply connectors 166 is connected to the cooling fluid inlet 158 of the single applicator and one of the plurality of cooling fluid return connectors 168 is connected to the cooling fluid outlet 160 of the single applicator. This will provide flow of cooling fluid through the single applicator. No cooling fluid will flow through any of the cooling fluid supply connectors or the cooling fluid return connectors that are not connected to the applicator. When a plurality of applicators is used, a separate one of the plurality of cooling fluid supply connectors 166 is connected to the cooling fluid inlet 158 of each of the plurality of applicators, and a separate one of the plurality of cooling fluid return connectors 168 is connected to the cooling fluid outlet 160 of each of the plurality of applicators. This will provide a cooling fluid supply connector 166 connected to each of the applicator cooling fluid inlets 158 and a cooling fluid return connector 168 connected to each of the applicator cooling fluid outlets 160 and thereby provide a flow of cooling fluid through each of the plurality of applicators attached to the system. Any number of applicators up to the number of cooling fluid supply connectors in the fluid supply system, here shown as three, can be connected to the fluid supply system. Again, no cooling fluid will flow through any of the cooling fluid supply connectors or the cooling fluid return connectors that are not connected to an applicator. This makes a fluid supply system that is very simple and easy to clinically use. The operator simply connects the mating fittings from the antenna to the matching type of connectors on the cooling fluid circulation system. The input and output have different type of connector fittings to avoid mistakes. The operator only need to connect the number of antennas that are to be used and the other unused fittings remain blocked to prevent loss of cooling fluid. The operator is not required to remove and discard any components or add components, but only to connect things together. The design also enables storage and sterilization of a cooling fluid circulation system that is made to fit all their applications providing much simplification in clinical utilization. The standard IV bags that form the fluid reservoir can be obtained already filled with sterile saline. The whole cooling fluid circulation system and fluid reservoir is delivered sterilized for use in surgical and interventional invasive procedures.

Figure 9:
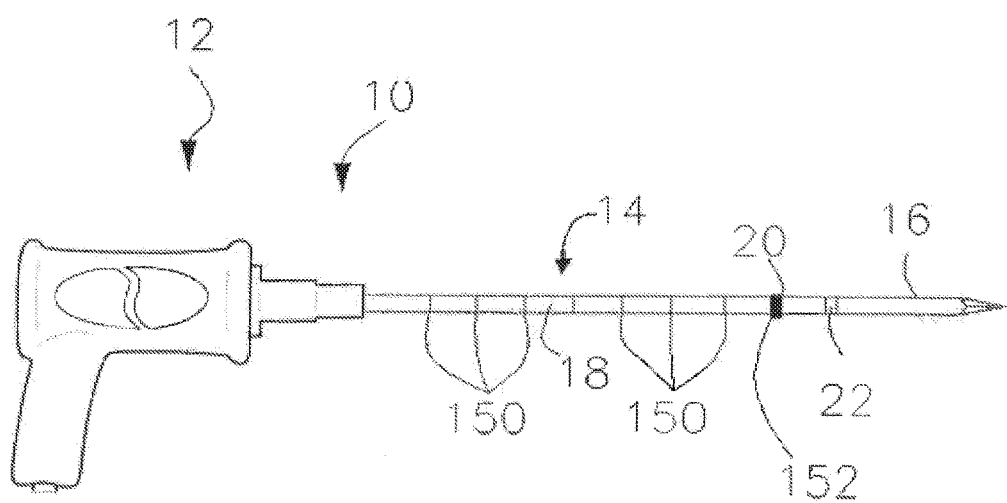
FIG. 9 is a side elevation of the applicator shown in FIG. 1, showing additional depth markings along the applicator.

In many cases, it is desirable to keep the microwave power on to the applicator as the applicator is withdrawn from the treatment site in the body when treatment of the diseased tissue is completed. This is because, in some instances, diseased tissue from the treatment site may be left along the insertion and withdrawal track which can seed additional diseased tissue growth. Further, in many body locations, removal of the applicator leaves an open wound along the insertion track which will bleed. Application of heat as the applicator is withdrawn provides coagulation of tissue and blood vessels that may prevent bleeding along the insertion track during withdrawal of the applicator from the treatment site. As shown in FIG. 9, a narrow separation gap 22 between the conductive applicator insertion tip 16 and the effective insertion end of the outer conductive sleeve 18, which is the insertion end of the shunt 20, provides a zone of high microwave intensity at the gap which can be effectively used to coagulate tissues along the insertion track if the microwave power is applied as the microwave antenna is withdrawn from the treated tissue. While methods of stepwise track ablation are known where the applicator is withdrawn in steps with microwave ablation heating performed at each step, and while it is known that track ablation can be performed with a continuous withdrawal of the applicator, effective continuous track ablation requires a substantially controlled constant preset withdrawal rate for the applicator. This is difficult to obtain when withdrawing an applicator.

As shown in FIG. 9, the applicator of the invention can be provided with depth marking 150 visible on the outside of the elongate applicator body at regular intervals along the elongate applicator body. The purpose of these markings is to provide an indication as to the depth of applicator penetration into the living body, and such markings are regularly spaced, such as every centimeter, along a portion of the length of the elongate applicator body where marks can be used to indicate depth of penetration. It has been found that these regularly spaced depth markings along the inserted shaft can be used to guide the rate of withdrawal of an applicator to provide effective coagulation of the insertion track. For this process, the system includes a sound generator that can generate a regular cadence sound. The sound generator may, for example, be part of the controller. By coordinating the cadence sounds with the amount of withdrawal of the applicator as indicated by the depth markings that appear as the applicator is withdrawn, the proper steady rate of withdrawal of the applicator can be obtained to assure uniform coagulation of tissues along inserted track. A typical desired rate of withdrawal of an applicator of the invention is approximately five mm per second at a sixty watt power level. So, for example, if the depth markings are spaced one cm apart along the inserted shaft, with a cadence that provides an audible signal, such as a beep, every second, the cadence sound provides a guide for the withdrawal at a rate of five mm for each audible beeping sound. This provides a rate of one cm every two seconds (every two beeps) to assure uniform coagulation of tissues during the withdrawal to reduce bleeding along the inserted track. This means that the applicator is withdrawn so that a depth mark appears every two beeps.

In addition to the regularly spaced depth markings, it has been found advantageous to also provide a warning marking 152, such as a red or other color marking, visible on the outside of the elongate applicator body at a position a known distance toward the attachment end of the applicator from the portion of the applicator that creates the tissue ablation (heating zone or zone of ablation). This distance, for example, could be about two to three cm from the attachment end of the heating zone (with the applicator shown, this will be about five cm from the insertion end of the applicator). As the applicator is withdrawn from the treated tissue, appearance of this warning marking indicates that the zone of tract ablation or coagulation is getting close to the outer skin surface (about two or three cm) so that withdrawal of the applicator can be stopped at a desired position short of the skin area to avoid damaging or coagulating tissue in the skin area. The physician withdrawing the applicator to perform track ablation is thus alerted to the closeness to the skin surface and can either stop the tract ablation at that time or only continue tract ablation for a short additional distance whichever, in the best judgment of the physician, will both provide adequate tract coagulation and also protect the skin surface.

While it is generally considered important to avoid or lessen as much as possible the sticking of tissue, such as heated coagulated or ablated tissue, to the applicator, it has been found that some sticking may be advantageous for fixing the position of the applicator in the tissue to be treated for the duration of the treatment. In an embodiment of the invention, the dielectric collar 22, such as shown in FIGS. 1, 2, 9, and 10, is left uncovered by material, such as a Teflon coating, that otherwise would cover the dielectric collar 22 to reduce tissue sticking, and the dielectric material is a material, such as PEEK (polyetheretherketone), that heated tissue will stick to. This is a relatively small area along the applicator, but upon heating, the tissue will stick to this dielectric material. This has the beneficial effect to secure the applicator to the tissue through the ablation procedure. This sticking occurs in about the first minute of the treatment period and helps to provide a secured positioning of the antenna relative to the target tissue so that the antenna stays in the intended location during the remainder of the treatment period which typically can be nine minutes or more. The PEEK material is a very high temperature thermoplastic with excellent chemical resistance. It has excellent mechanical properties with high flexural strength, impact resistance, tensile strength, is substantially rigid, and bonds well with epoxy. When removal of the applicator is desired (with the sticking there is a resistance to directly pulling the applicator straight out of the treated tissue, and such straight out removal is not recommended), the applicator can be rotated, such as through between thirty and forty-five degrees of rotation, which easily releases the sticking tissue to permit removal of the applicator.

Figure 12:
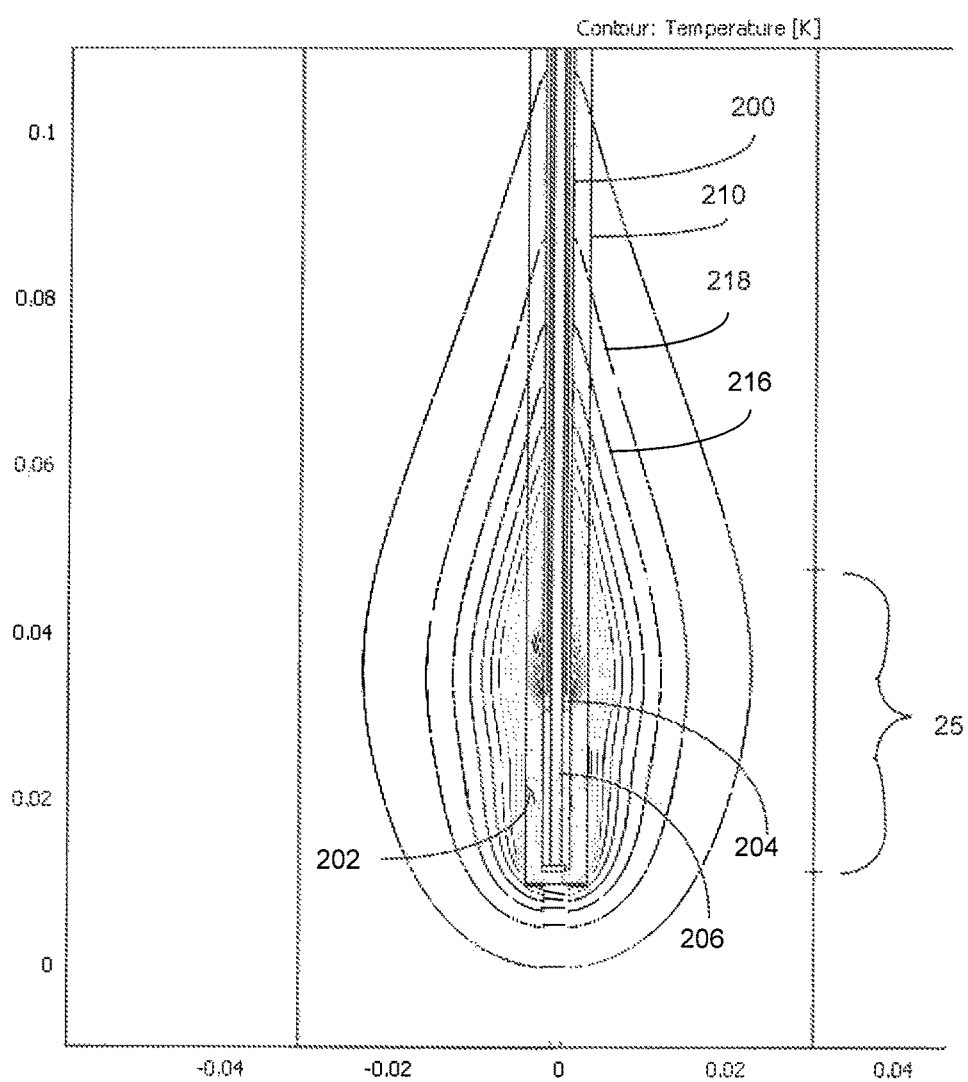
FIG. 12 is computer generated representation of a heating pattern produced by an applicator of the invention wherein the tissue along the proximal portion of the applicator is allowed to dry and char.

A limitation found in current microwave applicators that are used for microwave coagulation and ablation is that the energy distribution pattern generally extends back along the applicator from the proximal end of the desired coagulation and ablation zone around the microwave energy radiating portion of the applicator toward the proximal end of the applicator. This undesirably extends the coagulation and ablation zone along the applicator toward the proximal end of the applicator beyond the tissue desired to be coagulated or ablated, and forms what is referred to as a tail. This results in an elliptical or tear drop shaped energy distribution and heating pattern shape with a similarly shaped coagulation and ablation zone where the generally desired shape for the energy distribution pattern and the coagulation and ablation zone is generally more spherical. The inventors have theorized that this tail or extension of the heating pattern along the proximal portion of the applicator may be due, at least in part, to the drying of the tissue surrounding this proximal portion of the applicator as a result of the heating of the tissue, and that if the drying of the tissue can be reduced, the heated tail formed would also be reduced. As tissue is heated, moisture is driven from the tissue by the heat and the tissue dries. As the tissue dries, the dielectric constant of the tissue decreases and the heating of the tissue increases, further drying and eventually charring the tissue. While this heating and charring of the tissue is not a problem in the desired ablation zone since this ablates the tissue desired to be ablated, it is a problem when it extends the ablation zone into tissue not desired to be ablated. An example of this elongation of the heating zone which produces the heated tail is shown in FIG. 12. FIG. 12 is a numerical model created by the COMSOL computer modeling program of an expected heating pattern produced by a microwave applicator represented by cylinder 200 with a microwave radiating and desired heating zone 25 at the distal portion 202 of the applicator. Area 204 represents the dielectric collar, such as collar 22 in FIGS. 1, 2, and 10, and area 206 represents the conductive insertion tip 16 in FIGS. 1, 2, and 10. The heating pattern shown assumes overheating and drying to the point of charring of the tissue along the entire inserted length of the applicator represented by cylinder 210 surrounding applicator 200. The tissue dielectric is assumed constant at liver tissue values under normal conditions of $\in$=46.7 and σ=0.86 S/m with the surrounding cylinder 210 representing dried charred tissue at charred tissue values of $\in$=5.2 and σ=0.13 S/m. The proximal end of the applicator is at the top of FIG. 12 showing the extension of the heating zone extending toward the proximal end of the applicator and showing the teardrop shape of the heating zone.

Figure 13:
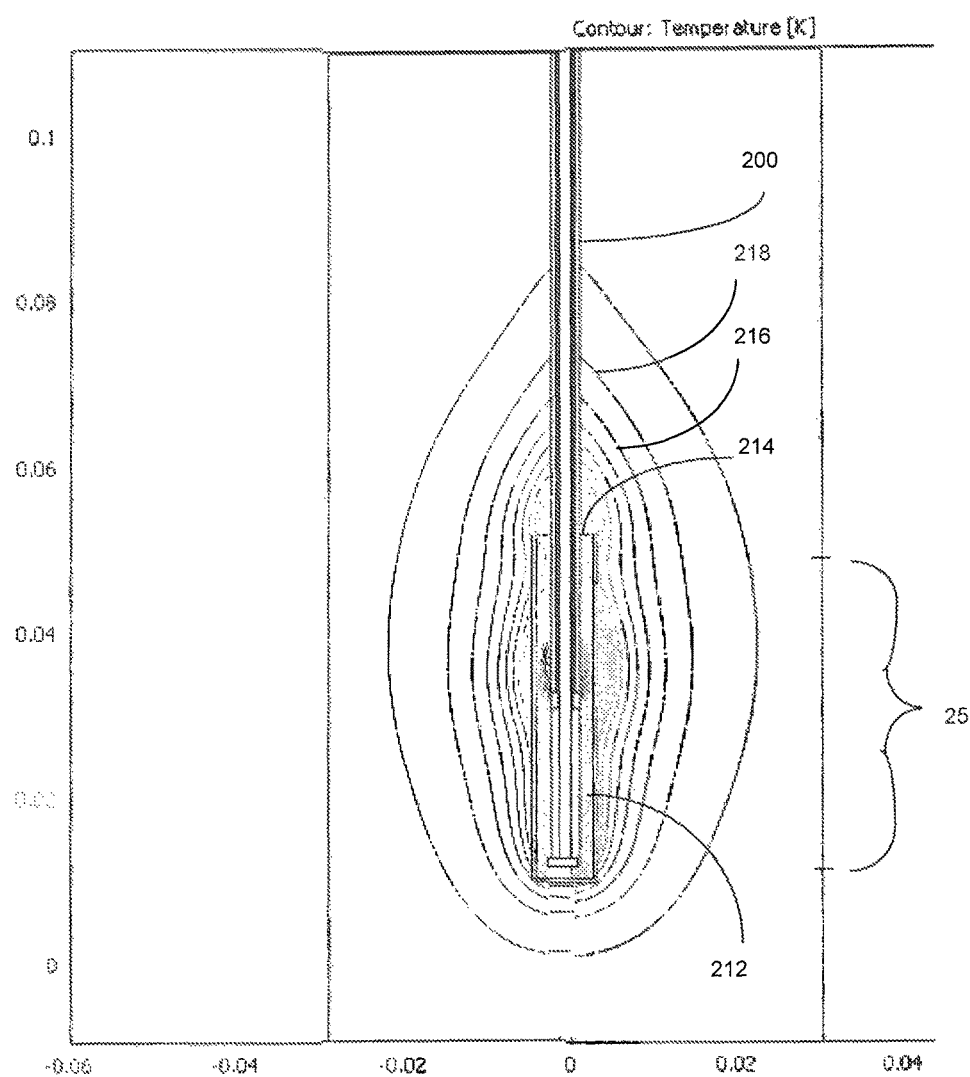
FIG. 13 is computer generated representation similar to that of FIG. 12 of a heating pattern produced by the same applicator of the invention as used for FIG. 12, wherein fluid is injected into the tissue along the proximal portion of the applicator to limit drying and charring of that tissue.

FIG. 13 is a numerical model created by the COMSOL computer modeling program of an expected heating pattern produced by the same microwave applicator represented by cylinder 200 with a microwave radiating and desired heating zone 25 at the distal portion 202 of the applicator. This heating pattern assumes overheating and drying to the point of charring of only the tissue along the desired heating zone represented by cylinder 212 (modeled as four centimeters in length) which extends just beyond each end of the microwave radiating zone 25 at the distal portion 202 of the applicator. This represents the situation where the tissue extending from the proximal end 214 of the desired heating zone 212 toward the proximal end of the applicator at the top of FIG. 13, referred to sometimes herein as the proximal tissue, remains moist and is not dried. Again, the tissue dielectric is assumed constant at liver tissue values under normal conditions of $\in$=46.7 and σ=0.86 S/m with the surrounding cylinder 212 representing dried charred tissue at charred tissue values of $\in$=5.2 and σ=0.13 S/m.

A comparison of FIGS. 12 and 13, shows the heating pattern in FIG. 13 where the proximal tissue remains moist is shorter and more spherical in shape with much less of a tail toward the proximal end of the applicator than the heating pattern of FIG. 12 in which the proximal tissue dries out. In the models, the contour line 216 representing a calculated model temperature of about 340 degrees K in FIG. 12 is 6.6 cm compared to 6.1 cm in FIG. 13, and contour line 218 representing a calculated model temperature of about 328 degrees K in FIG. 12 is 8.1 cm compared to 6.8 cm in FIG. 13. These Figs. support the inventors' theory that the elongation of the heating pattern is in part due to the heating and drying of the proximal tissue. Therefore, if the proximal tissue is kept hydrated during treatment, the heating pattern produced is a more desirable spherical heating pattern than the heating pattern produced when the tissue is not kept hydrated.

Figure 14:
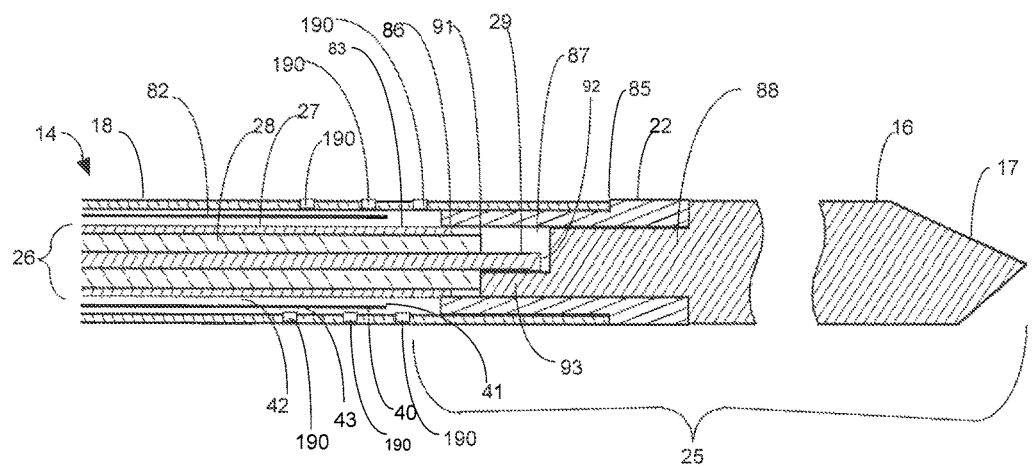
FIG. 14 is a vertical section similar to that of FIG. 10 of a different embodiment of applicator of the invention with fluid injection ports.

FIG. 14 is a vertical section of the applicator of FIG. 10 additionally including one or more small openings, holes, or slots 190 extending through the outer conductive sleeve 18 which allow a portion of the fluid circulating in the cooling fluid space 82 of applicator 14 to flow through outer conductive sleeve 18 of applicator 14 and be injected into the tissue surrounding the outer conductive sleeve in the area of the openings 190. The openings 190 are positioned to inject cooling fluid into the tissue in a region of the tissue starting at approximately the proximal end of the desired heating area 25 (the end of the desired heating area or primary energy radiation zone toward the attachment or proximal end of the applicator) and extending a distance toward the attachment or proximal end of the applicator represented by the handle in FIG. 1. The distance along the applicator from the proximal end of the desired heating area 25 toward the proximal end of the applicator that fluid injection extends and the number of openings and arrangement of the openings around the conductive outer sleeve 18 is a distance, number, and arrangement determined to be effective to reduce or limit drying of the tissue and reduce or limit the extent of the elongation of the heating pattern a desired amount compared to the elongation of the heating pattern produced by the particular applicator under similar operating conditions without the injection of the fluid. This hydrated tissue will be referred to as the proximal tissue adjacent the desired heating zone. The purpose of injecting a portion of the cooling fluid circulating in the applicator into the tissue is not to directly cool the proximal tissue adjacent the desired heating zone with the fluid, but to hydrate or wet the proximal tissue adjacent the desired heating zone so it does not dry. This hydrating of the proximal tissue counteracts the drying of the tissue that would otherwise occur and tends to maintain the normal dielectric constant of this proximal tissue. This reduces the amount of microwave energy that travels down the proximal portion of the applicator, which in FIG. 14, reduces the amount of microwave energy that travels from the desired heating zone down outer conductive sleeve 18.

Figure 15:
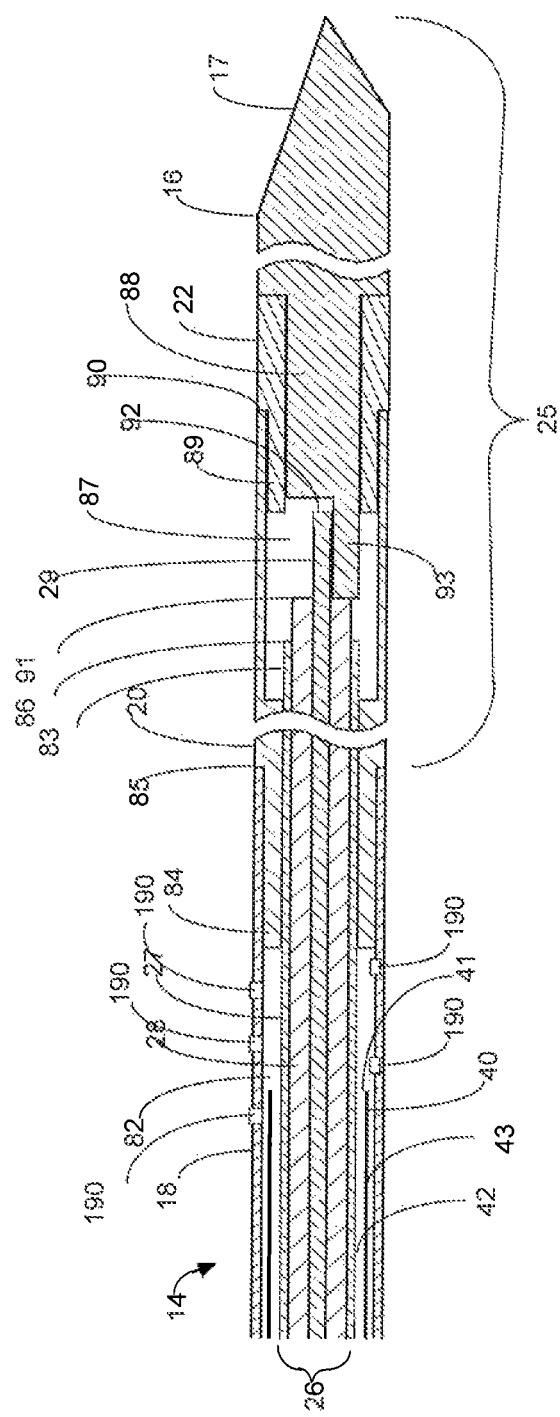
FIG. 15 is a vertical section similar to that of FIG. 2 of a different embodiment of applicator of the invention with fluid injection ports.

FIG. 15 is a vertical section of the applicator of FIG. 2, which includes the conductive shunt 20 between the dielectric collar 22 and the outer conductive sleeve 18, and additionally includes the one or more small openings, holes, or slots 190 extending through the outer conductive sleeve 18 as shown in FIG. 14, which allow a portion of the fluid circulating in the cooling fluid space 82 of applicator 14 to flow through outer conductive sleeve 18 of applicator 14 and be injected into the proximal tissue adjacent the desired heating zone. While the arrangement of the openings extending through the outer conductive sleeve 18 are spaced a short distance from the immediate proximal end of the desired heating zone 25, this is still considered for purposes of the invention to be at the approximate proximal end of the desired heating zone. Further, usually the fluid injected into the tissue will spread some from the openings toward the immediate proximal end of the desired heating zone 25. While the short distance shown from the immediate proximal end of the desired heating zone 25 may allow the heating zone to expand a short distance toward the proximal end of the applicator, this short distance generally will not be significant. If desired, the reduced outer diameter end portion 84 of shunt 20 could be shortened to allow openings through the outer conductive sleeve 18 to be positioned closer to the immediate proximal end of the desired heating zone 25 or passages could be provided in the reduced outer diameter end portion 84 of shunt 20 leading to openings through outer conductive sleeve 18 closer to the immediate proximal end of the desired heating zone 25.

The embodiments of FIGS. 14 and 15 maintain the circulation of the cooling fluid into and out of the applicator and through the applicator cooling fluid space 82, however there will be less fluid flowing from the applicator through the fluid return than is supplied the applicator. A fluid circulation system such as shown in FIG. 11 can be used to supply the cooling fluid to the applicator and receive the return flow of cooling fluid from the applicator. In such instance, fluid pump 170 will generally provide sufficient hydraulic pressure to force a small amount of fluid through the openings 190 in the outer conductive sleeve 18 into the tissue to keep the proximal tissue adjacent the desired heating zone hydrated. The typical flow rate of cooling fluid in the cooling fluid space within the illustrated applicator body is in the range of 20 to 40 ml/minute. The rate needed to infuse fluid into the tissue in the inserted proximal portion of the applicator is generally less than 10 ml/minute and typically in the range of 1 to 6 ml/minute. Pump 170 in the fluid circulation system of FIG. 11 can generally be chosen to provide ample flow to the number of applicators connected to the fluid circulation system to permit the small volume to pass into the tissue while maintaining cooling circulation through the applicator. If desired or necessary, particularly when a large variable number of applicators can be attached to the fluid circulation system, such as more than the three possible with the system shown, pressure and/or flow sensors and a pump controller can be provide to measure and maintain the pressure and/or flow rate of the fluid supplied to connected applicators sufficient to ensure desired fluid injection to the proximal tissue adjacent the desired heating zone through the connected applicators when a large number of applicators are connected to the fluid circulation system without providing too much pressure and fluid injection when only one or a few applicators are connected to the fluid circulation system.

Figure 16:
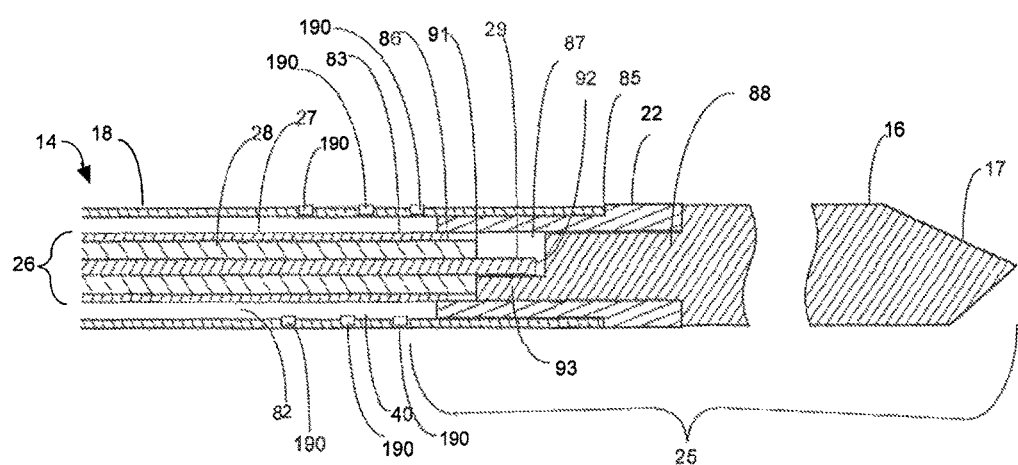
FIG. 16 is a vertical section similar to that of FIGS. 10 and 14 of a different embodiment of applicator of the invention with fluid injection ports and without a cooling fluid return path.

In a further embodiment of the applicator, the infusion of fluid into the proximal tissue adjacent the desired heating zone from the fluid flow space in the applicator may be provided by eliminating the fluid flow return path from the applicator, either by blocking the fluid return path or by removing the fluid return path inside the applicator body and providing a lower flow rate of cooling fluid to the applicator, such as by providing either a lower flow rate fluid pump or by providing a fluid gravity drip line that is typical if intravenous (IV) fluid applications. FIG. 16 is a vertical section similar to that of FIG. 10 but without a cooling fluid outlet and without the guide sleeve 40, and additionally including the one or more small openings, holes, or slots 190 extending through the outer conductive sleeve 18 as shown in FIG. 14. However, in this embodiment of the applicator, the flow of cooling fluid into and through the cooling fluid space 82 is limited to the fluid that flows through the openings 190 into the proximal tissue adjacent the proximal end of the desired heating zone. Again, the purpose of injecting fluid into the proximal tissue adjacent the desired heating zone is to hydrate or wet the proximal tissue adjacent the desired heating zone so it does not dry. This hydrating of the proximal tissue counteracts the drying of the tissue that would otherwise occur and tends to maintain the normal dielectric constant of this proximal tissue. This reduces the amount of microwave energy that travels down the proximal portion of the applicator, which in FIG. 16, reduces the amount of microwave energy that travels from the desired heating zone down the outer conductive sleeve 18. With this embodiment, the cooling of the applicator by the cooling fluid flowing through the cooling fluid space 82 along the outside of coaxial transmission line 26 and the inside of outer conductive sleeve 18 is significantly reduced from the cooling provided in the embodiments of FIGS. 10 and 14 since the flow of cooling fluid is significantly reduced. As indicated, the typical flow rate within the applicator body of FIGS. 10 and 14 having a fluid inlet and a fluid outlet is in the range of 20 to 40 ml/minute. The rate needed to infuse fluid into the proximal tissue adjacent the desired heating zone is less than 10 ml/minute and typically in the range of only 1 to 6 ml/minute. Therefore, it is only the significantly less flow in the range of 1 to less than 10 ml/minute of cooling fluid that flows through the cooling fluid space 82. However, for many applications of the applicator, this is all that is needed during treatment.

Figure 17:
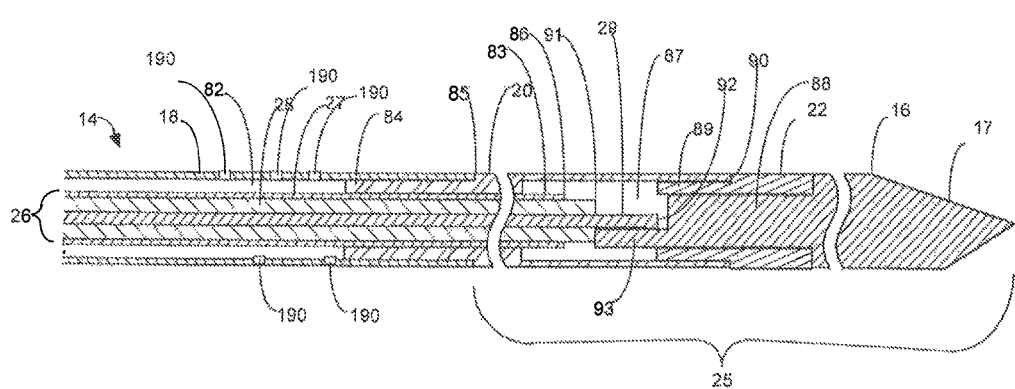
FIG. 17 is a vertical section similar to that of FIGS. 2 and 15 of a different embodiment of applicator of the invention with fluid injection ports and without a cooling fluid return path.

FIG. 17 is a vertical section similar to that of FIG. 2, but without a cooling fluid outlet and without the guide sleeve 40, and additionally including the one or more small openings, holes, or slots 190 extending through the outer conductive sleeve 18 as shown in FIG. 15. Again, as with the embodiment of FIG. 16, in this embodiment of the applicator, the flow of cooling fluid into and through the cooling fluid space 82 is limited to the fluid that flows through the openings 190 into the proximal tissue adjacent the proximal end of the desired heating zone. As with the embodiment of FIG. 15, if desired, the reduced outer diameter end portion 84 of shunt 20 could be shortened to allow openings through the outer conductive sleeve 18 to be positioned closer to the immediate proximal end of the desired heating zone 25 or passages could be provided in the reduced outer diameter end portion 84 of shunt 20 leading to openings through outer conductive sleeve 18 closer to the immediate proximal end of the desired heating zone 25.

Figure 18:
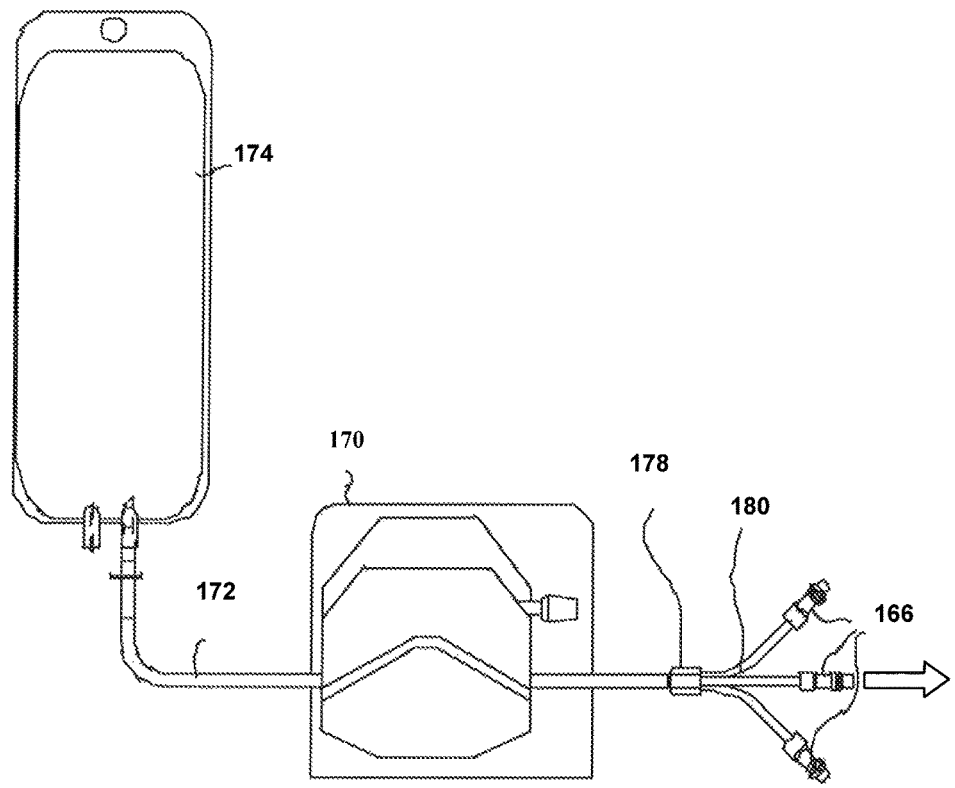
FIG. 18 is a schematic representation of a cooling fluid circulation system of the invention similar to that of FIG. 11, but without the fluid return line and fluid return connectors, and usable with the applicators of FIGS. 17 and 18.

Since the flow rate of fluid to the applicators of FIGS. 16 and 17 is reduced to only that needed for hydration of the proximal tissue adjacent the desired heating zone, i.e., in the range of 1 to less than 10 ml/minute, the fluid supply systems used to supply fluid to such applicators need only to supply fluid at the reduced flow rate, and do not need provision to accept return fluid from the applicators. FIG. 18 is a schematic representation showing a fluid supply system similar to that of FIG. 11, but without the cooling fluid return line 186 and the cooling fluid return connectors 168. Fluid pump 170 is selected to supply cooling fluid at the lower flow rate, typically between about 1 and less than 10 ml/minute, rather than the 20 to 40 ml/minute provided by the pump of FIG. 11. Further, since control of injected fluid may be more critical with only fluid injection than with fluid flow through the cooling fluid space 82 with return to the fluid reservoir, and particularly when a large variable number of applicators can be attached to the fluid circulation system, such as more than the three possible with the system shown, pressure and/or flow sensors and a pump controller can be provide to measure and maintain the pressure and/or flow rate of the fluid supplied to connected applicators sufficient to ensure desired fluid injection to the proximal tissue adjacent the desired heating zone through the connected applicators when a large number of applicators are connected to the fluid circulation system without providing too much pressure and fluid injection when only one or a few applicators are connected to the fluid circulation system. It should be noted that since the fluid supply system of FIG. 11 includes cooling fluid return connectors 168 which include one way valves so are blocked if no cooling fluid outlet connectors are connected thereto, such system of FIG. 11 would operated similarly to that of FIG. 18 and could be used in place of the system of FIG. 18 for the applicators of FIGS. 16 and 17 with only adjustment of the fluid output pressure and/or flow rate, if necessary.

Figure 19:
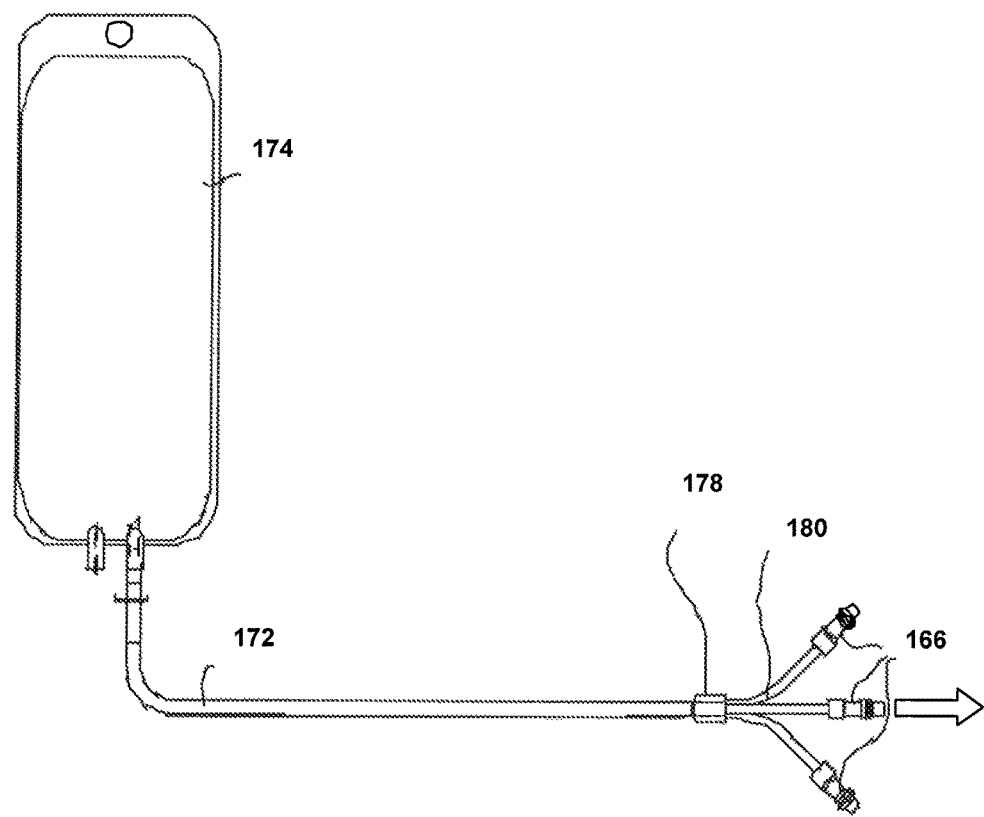
FIG. 19 is a schematic representation of a cooling fluid circulation system of the invention without the fluid return line, fluid return connectors, and fluid pump, and usable with the applicators of FIGS. 17 and 18.

FIG. 19 is a schematic representation showing a fluid supply system without a pump or cooling fluid return line and cooling fluid return connectors. The fluid supply system of FIG. 19 uses a fluid gravity drip line that is typical of intravenous (IV) fluid applications. In such a case the fluid flow rate from the gravity drip line can be set to a predetermined flow rate that would provide the typically desired flow rate in the range of 1 to 6 ml/minute of fluid flow to each of the applicators attached to the fluid supply system. Such flow rate from the fluid reservoir (IV bag) would be adjusted each time the number of applicators attached to the system is changed.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. A microwave applicator for insertion into living body tissue for heat treatment of diseased tissue within the living body tissue, the microwave applicator comprising:
    an elongate applicator body having an insertion end for insertion into a tissue region of the living body and an attachment end for attachment to a source of microwave energy;
    an antenna for radiating microwave energy disposed toward the insertion end of the elongate applicator body, said antenna, when radiating microwave energy, creating a primary energy radiation zone;
    a microwave energy transmission line disposed within the elongate applicator body to conduct the microwave energy from the attachment end of the elongate applicator body to the antenna, said microwave energy transmission line having an inner conductor and an outer conductor;
    an outer electrically conductive sleeve extending around and spaced from the outer conductor of the microwave energy transmission line to form an outside of a portion of the elongate applicator body and to provide a cooling fluid space between the outer conductor of the microwave transmission line and an inside surface of the outer electrically conductive sleeve;
    a cooling fluid in the cooling fluid space;
    an electrically conductive applicator tip forming the insertion end of the elongate applicator body and electrically coupled to the inner conductor of the transmission line;
    dielectric material positioned between and joining the outer electrically conductive sleeve and the electrically conductive applicator tip to electrically insulate the electrically conductive applicator tip from the outer electrically conductive sleeve and from the outer conductor of the microwave transmission line so that the electrically conductive applicator tip is electrically insulated from the outer electrically conductive sleeve and from the outer conductor of the microwave transmission line, and
    a plurality of openings extending through the outer electrically conductive sleeve from the cooling fluid space for injecting the cooling fluid from the cooling fluid space into an area of tissue to be hydrated surrounding the elongate applicator body and selectively positioned adjacent to the elongate applicator body extending along the elongate applicator body from approximately adjacent to the end of the primary energy radiation zone toward the attachment end of the elongate applicator body;

wherein the cooling fluid circulates into and out of the cooling fluid space and the plurality of openings thereby limiting a tail of the primary energy radiation zone causing formation of a substantially spherical ablation zone.

2. A microwave applicator for insertion into living body tissue, according to claim 1, additionally including a guide sleeve positioned concentrically around and spaced from the outer conductor of the microwave energy transmission line and the inside surface of the outer electrically conductive sleeve to divide at least a portion of the cooling fluid space into an inner cooling fluid space along the outer conductor of the microwave energy transmission line and an outer cooling fluid space along the inside surface of the outer electrically conductive sleeve, said inner cooling fluid space communicating with said outer cooling fluid space whereby said guide sleeve is adapted to guide flow of the cooling fluid within the cooling fluid space to cool the microwave energy transmission line and the outer electrically conductive sleeve.

3. A microwave applicator for insertion into living body tissue according to claim 2, wherein the dielectric material extends between the outer electrically conductive sleeve and the outer conductor of the coaxial microwave transmission line to form an end of the cooling fluid space toward the insertion end of the applicator.

4. A microwave applicator for insertion into living body tissue according to claim 3, wherein the cooling fluid space terminates along the length of the microwave energy transmission line prior to reaching the antenna.

5. A microwave applicator for insertion into living body tissue according to claim 2, additionally including an electrically conductive shunt extending between the outer electrically conductive sleeve and the outer conductor of the coaxial microwave transmission line to form an end of the cooling fluid space toward the insertion end of the applicator and forming an extension of the outer electrically conductive sleeve, the dielectric material being positioned between and joining the electrically conductive shunt and the electrically conductive tip to electrically insulate the electrically conductive tip from the electrically conductive shunt, the outer electrically conductive sleeve, and the outer conductor of the microwave transmission line.

6. A microwave applicator for insertion into living body tissue according to claim 5, wherein the cooling fluid space terminates along, the length of the microwave energy transmission line prior to reaching the antenna.

7. A microwave applicator for insertion into living body tissue according to claim 2, additionally including a handle from which the outer electrically conductive sleeve, microwave energy transmission line, and the guide sleeve extend.

8. A microwave applicator for insertion into living body tissue according to claim 7, wherein the handle includes an inlet for connection to a source of cooling fluid and an outlet for outflow of the cooling fluid, and wherein, when the cooling fluid is supplied through the cooling fluid inlet, the cooling fluid flows into the cooling fluid space in the elongate applicator body from the handle and a portion thereof returns from the cooling fluid space in the elongate applicator body into the handle.

9. A microwave applicator for insertion into living body tissue according to claim 8, additionally including a cooling fluid circulation system having at least one fluid supply connector adapted to be connected to the cooling fluid inlet and at least one fluid return connector adapted to be connected to the cooling fluid outlet, said at least one fluid supply connector including a normally closed shut off valve which opens when connected to the cooling fluid inlet and the at least one fluid return connector including a one way flow valve allowing flow only into the at least one fluid return connector.

10. A microwave applicator for insertion into living body tissue according to claim 1, additionally including a handle from which the outer electrically conductive sleeve and the microwave energy transmission line extend, and wherein the handle includes an inlet for connection to a source of cooling fluid, and wherein, when the cooling fluid is supplied through the cooling fluid inlet, the cooling fluid flows into the cooling fluid space in the elongate applicator body from the handle and at least a portion thereof flows from the cooling fluid space in the elongate applicator body through the one or more openings into the tissue to be hydrated.

11. A microwave applicator for insertion into living body tissue according to claim 10, additionally including a cooling fluid circulation system having at least one fluid supply connector adapted to be connected to the cooling fluid inlet, said at least one fluid supply connector including a normally closed shut off valve which opens when connected to the cooling fluid inlet to allow flow of fluid into the cooling fluid inlet.

12. A microwave applicator for insertion into living body tissue according to claim 1, wherein the elongate applicator body includes an inlet for connection to a source of cooling fluid, and wherein, when the cooling fluid is supplied through the cooling fluid inlet, the cooling fluid flows into the cooling fluid space in the elongate applicator body and at least a portion thereof flows from the cooling fluid space in the elongate applicator body through the one or more openings into the tissue to be hydrated.

13. A microwave applicator for insertion into living body tissue according to claim 1, wherein the electrically conductive applicator tip is metal.

14. A microwave applicator for insertion into living body tissue according to claim 13, wherein the electrically conductive applicator tip is stainless steel.

15. A microwave applicator for insertion into living body tissue according to claim 13, wherein the electrically conductive applicator tip is brass.

16. A microwave applicator for insertion into living body tissue according to claim 1, wherein the outer electrically conductive sleeve is metal.

17. A microwave applicator for insertion into living body tissue according to claim 16, wherein the outer electrically conductive sleeve is stainless steel.

18. A system for microwave therapy for heat treatment of diseased tissue within a living body, comprising:
 a microwave applicator for insertion into living body tissue, according to claim 1; and
 a fluid reservoir in communication with the cooling fluid space to supply the cooling fluid to the cooling fluid space, said fluid reservoir positioned and adapted to allow fluid to flow by gravity from the fluid reservoir to the cooling fluid space.

19. A system for microwave therapy for heat treatment of diseased tissue within a living body, according to claim 18, wherein the fluid reservoir is a standard fluid filled IV bag with a fluid gravity drip line.

20. A system for microwave therapy for heat treatment of diseased tissue within a living body, comprising:
 a microwave applicator for insertion into living body tissue, according to claim 1;
 a fluid reservoir; and
 a pump to pump fluid from the fluid reservoir to the cooling fluid space.

* * * * *